United States Patent
Ohtaki et al.

(10) Patent No.: US 7,906,599 B2
(45) Date of Patent: Mar. 15, 2011

(54) TRANSITION METAL COMPOUND, CATALYST FOR OLEFIN POLYMERIZATION CONTAINING THE SAME, AND METHOD FOR PRODUCING PROPYLENE/ETHYLENE-α-OLEFIN BLOCK COPOLYMER BY USING THE CATALYST

(75) Inventors: Hisashi Ohtaki, Yokohama (JP); Naoshi Iwama, Yokkaichi (JP); Masami Kashimoto, Yokohama (JP); Tomohiro Kato, Yokohama (JP); Tsutomu Ushioda, Yokkaichi (JP)

(73) Assignee: Japan Polypropylene Corporation, Tokyo (JP)

( * ) Notice: Subject to any disclaimer, the term of this patent is extended or adjusted under 35 U.S.C. 154(b) by 0 days.

(21) Appl. No.: 12/297,444

(22) PCT Filed: Apr. 17, 2007

(86) PCT No.: PCT/JP2007/058322
§ 371 (c)(1), (2), (4) Date: Oct. 17, 2008

(87) PCT Pub. No.: WO2007/123110
PCT Pub. Date: Nov. 1, 2007

(65) Prior Publication Data
US 2009/0099310 A1 Apr. 16, 2009

(30) Foreign Application Priority Data

Apr. 19, 2006 (JP) ................................. 2006-116233
Feb. 8, 2007 (JP) ................................. 2007 028706

(51) Int. Cl.
*C08F 4/76* (2006.01)
*C08F 4/64* (2006.01)
*C07F 17/00* (2006.01)

(52) U.S. Cl. ........ 526/160; 526/170; 526/126; 526/941; 526/943; 526/65; 526/901; 526/348; 556/53; 556/51; 502/103

(58) Field of Classification Search .................... 556/53; 526/170, 943, 160
See application file for complete search history.

(56) References Cited

U.S. PATENT DOCUMENTS

| | | | | |
|---|---|---|---|---|
| 6,255,515 B1 * | 7/2001 | Kato et al. | ..................... | 556/478 |
| 2004/0162403 A1 * | 8/2004 | Shimizu et al. | ............... | 526/160 |
| 2006/0178486 A1 * | 8/2006 | Suzuki et al. | ................. | 525/242 |

FOREIGN PATENT DOCUMENTS

| | | |
|---|---|---|
| JP | 60 130604 | 7/1985 |
| JP | 3 234709 | 10/1991 |
| JP | 4 100808 | 4/1992 |
| JP | 4 337308 | 11/1992 |
| JP | 5 247128 | 9/1993 |
| JP | 6 192500 | 7/1994 |
| JP | 6 192506 | 7/1994 |
| JP | 9 316145 | 12/1997 |
| JP | 9 316147 | 12/1997 |
| JP | 10 158351 | 6/1998 |
| JP | 10 226712 | 8/1998 |
| JP | 11 228648 | 8/1999 |
| JP | 11 240909 | 9/1999 |
| JP | 11 240929 | 9/1999 |
| JP | 2000 95791 | 4/2000 |
| JP | 2003 292700 | 10/2003 |
| JP | 2004 2310 | 1/2004 |
| JP | 2004-2310 A * | 1/2004 |
| JP | 2004 155739 | 6/2004 |
| JP | 2005-336092 A * | 12/2005 |
| WO | 95 27740 | 10/1995 |
| WO | 2004 087775 | 10/2004 |
| WO | 2005 005503 | 1/2005 |
| WO | WO 2005/005503 A1 * | 1/2005 |
| WO | 2005 023890 | 3/2005 |
| WO | 2005 023891 | 3/2005 |
| WO | 2005 023892 | 3/2005 |

OTHER PUBLICATIONS

Sato et al., JP 2004-2310 (Jan. 2004); abstract and translation in English.*
Sato et al., JP 2005-336092 (Dec. 2005); abstract and translation in English.*

(Continued)

Primary Examiner — Rip A. Lee
(74) Attorney, Agent, or Firm — Oblon, Spivak, McClelland, Maier & Neustadt, L.L.P.

(57) ABSTRACT

Disclosed is a novel transition metal compound which is used for forming a metallocene catalyst for olefin polymerization. Specifically disclosed is a novel transition metal compound represented by the general formula below which enables to form a metallocene catalyst that has a balanced reactivity with ethylene and a comonomer selected from α-olefins having 3-20 carbon atoms and enables to produce an α-olefin polymer having a high molecular weight. Also specifically disclosed are a catalyst for olefin polymerization containing such a transition metal compound, and a method for producing a propylene/ethylene-α-olefin block copolymer wherein such a catalyst is used.

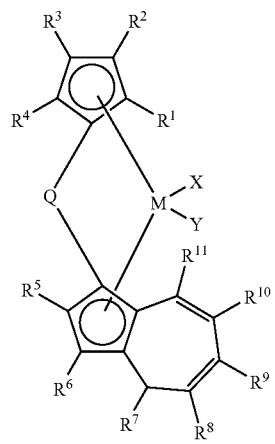

15 Claims, No Drawings

OTHER PUBLICATIONS

Fan, W. et al., "Alternating Stereospecific Copolymerization of Ethylene and Propylene With Metallocene Catalysts", J. Am. Chem. Soc., vol. 123, No. 39, pp. 9555-9563 (2001).

Shin, Y-W. et al., "Synthesis and Characterization of Ethylene-Propylene Random Copolymers with Isotactic Propylene Sequence", Polymer, vol. 42, pp. 9611-9615 (2001).

* cited by examiner

TRANSITION METAL COMPOUND, CATALYST FOR OLEFIN POLYMERIZATION CONTAINING THE SAME, AND METHOD FOR PRODUCING PROPYLENE/ETHYLENE-α-OLEFIN BLOCK COPOLYMER BY USING THE CATALYST

CROSS-REFERENCE TO RELATED APPLICATIONS

The present application is a 35 U.S.C. §371 National Stage patent application of International patent application PCT/JP2007/058322, filed on Apr. 17, 2007, which claims priority to Japanese patent applications JP 2007-028706, filed on Feb. 8, 2007 and JP 2006-116233, filed on Apr. 19, 2006.

BACKGROUND OF THE INVENTION

1. Field of the Invention

The present invention relates to a new transition metal compound, a catalyst for olefin polymerization containing this transition metal compound and a method for producing a propylene/ethylene-α-olefin block copolymer using this catalyst for olefin polymerization, more particularly relates to a new transition metal compound constituting a catalyst for olefin polymerization in a metallocene type catalyst, that is, a new transition metal compound, which can form the metallocene type catalyst that has well-balanced reactivity between ethylene and a comonomer selected from α-olefins having 3 to 20 carbon atoms and produces an α-olefin polymer (hereinafter, may be referred to as CP) of a high molecular weight, and a catalyst for olefin polymerization containing this transition metal compound, and a method for producing a propylene/ethylene-α-olefin block copolymer using this catalyst for olefin polymerization.

2. Description of the Prior Art

A polypropylene based resin material is broadly used and is given important post as an industrial material because of its many excellent performance mainly such as moldability, various properties, economical efficiency and environmental issues adaptability.

A polypropylene based resin material is so important in industrial fields that further improvement of its performance has been ever pursued in many aspects. In order to improve its flexibility and impact resistance, for example, a method for adding an elastomer such as ethylene-propylene rubber to a propylene homopolymer or a method for producing a so-called block copolymer by multistage polymerization where propylene and ethylene are copolymerized subsequently after homopolymerization of propylene, have been carried out.

While such a polypropylene based resin material is industrially produced mainly with a conventional Ziegler-Natta type catalyst and a metallocene type catalyst, there are many problems to be solved therein.

For example, a propylene based block copolymer obtained by polymerization in the presence of a conventional Ziegler-Natta type catalyst necessarily contains a low molecular weight component (oligomer component etc.), due to the catalyst properties, which not only causes generation of smoke and malodor during processing, but also poses various problems such as bad odor effect and deterioration of anti-blocking property due to sticking even after processing.

In contrast, it has been known for a long time that highly isotactic polypropylene can be obtained by polymerizing propylene using a metallocene type catalyst different from a conventional Ziegler-Natta type catalyst. It is also disclosed that a so-called block copolymer is produced by multistage polymerization (see, for example, Patent Document 1), and further, a propylene-ethylene block copolymer having high stiffness and impact resistance is produced using a metallocene type catalyst (see, for example, Patent Documents 2 and 3).

Although a metallocene type catalyst is characterized by having generally higher polymerization activity compared with a conventional Ziegler-Natta type catalyst and providing a polymer having a narrow molecular weight distribution and a uniform distribution of copolymer compositions, it has still many problems to be solved such as a economical problem due to use of a metallocene compound to be synthesized in a complicated process and use of MAO as well as necessity for improving polymerization activity, molecular weight and stereoregularity of a polymer.

And, various researches for improving a metallocene type catalyst have been continued from various standpoints, for example, a transition metal compound that provides polypropylene having a high melting point is disclosed in order to improve stiffness of a propylene-ethylene block copolymer (see, for example, Patent Documents 4 and 5), however, there is a problem that the reactivity of ethylene is lower compared with that of propylene when propylene and ethylene are copolymerized using a catalyst composed of these transition metal compounds. In other words, it is necessary to polymerize with feeding a gas of a much deviated monomer ratio from the content in a copolymer in order to obtain the copolymer having a desired content of ethylene, it has a problem on producing, further, a copolymer having a desired content can not sometimes be produced in an extreme case.

Although it has been shown that the reactivity of propylene and the reactivity of ethylene can be changed by changing a transition metal compound to be used (see, for example, Patent Document 6 and Non-patent Document 1), transition metal compound that fills sufficient balance of the reactivity of both compounds has not been known so far, and especially when copolymerization of propylene and ethylene is carried out in a gas phase, transition metal compound that fills the reactivity of both compounds with sufficient balance has not been known so far.

In addition, for example, it is necessary for a propylene-ethylene block copolymer to show a low glass transition temperature in order to attain a high impact resistance, it is preferable that the content of each of propylene and ethylene in the copolymer satisfies the specific range in order to satisfy this (see, for example, Non-patent Document 2). Therefore, as the property of catalyst in production, it is necessary that the reactivity of propylene and the reactivity of ethylene has a good balance and is in a specific range respectively.

Further, when a known transition metal compound is used, it poses a problem that the obtained copolymer has a low molecular weight in the case of gas phase copolymerization of propylene and ethylene. In order to attain high impact resistance in a propylene-ethylene block copolymer, it is necessary for a molecular weight of copolymer to have a value over a specific level, and thus a transition metal compound and a catalyst that can produce a copolymer having a higher molecular weight are desired.

Still more, in order to improve impact resistance of polypropylene, it is also disclosed the improvement of impact resistance by blending ethylene-higher α-olefin rubber (the α-olefin has 4 to 8 carbon atoms) (see, for example, Patent Documents 7 and 8).

Such a rubber copolymer, however, has a shape difficult to handle depending on its composition and causes troubles in blending operation such as a trouble that it can not be pelletized unlike a crystalline resin. In the case of so-called polymer blending, wherein a rubber copolymer is added to polypropylene, the rubber copolymer is not dispersed sufficiently, which makes it difficult to attain high stiffness and impact resistance at the same time.

A method for producing an ethylene-higher α-olefin rubber such as an ethylene-butene rubber (EBR) and an ethylene-octene rubber (EOR) in multistage polymerization is also known. For example, a method for producing a propylene/ethylene-α-olefin block copolymer excellent in stiffness and impact resistance by carrying out multistage polymerization using a metallocene catalyst is disclosed (see, for example, Patent Documents 9 to 11).

Liquid-phase polymerization using a solvent, however, has a problem that efficient production is difficult because a formed CP dissolves in the solvent resulting in necessity for the solvent to be distilled off in order to separate the polymer.

Gas phase polymerization for producing a CP portion by using a specific transition metal compound is also disclosed (see, for example, Patent Documents 12 to 15).

A method using these specific transition metal compounds, however, has a problem that a CP having a sufficiently high molecular weight can not be produced in the industrially feasible range of temperature/pressure.

While stiffness and impact resistance have been improved to a certain extent by the above disclosed inventions, there is still a room for improvement in the molecular weight and the comonomer composition of an ethylene-α-olefin copolymer providing higher impact resistance. A method for stably and efficiently producing a propylene/ethylene-α-olefin block copolymer containing the copolymer that can satisfy the above properties has been desired to be developed.

In view of the above described background arts, a metallocene type polymerization catalyst, which is important and essential for the industrial production of a polypropylene based resin material broadly and conveniently used in many industrial fields has still many problems therein. One important problem among the above problems is that the reactivity of ethylene and the reactivity of an α-olefin having 3 to 20 carbon atoms do not balance in the copolymerization of the ethylene and the α-olefin having 3 to 20 carbon atoms resulting in difficulty in obtaining high molecular weight. An object of the present invention intends to solve such problems and to develop a metallocene type catalyst for α-olefin polymerization that shows balanced reactivity of ethylene and an α-olefin having 3 to 20 carbon atoms and gives a copolymer of a high molecular weight.

Patent Document 1: JP-A-4-337308
Patent Document 2: JP-A-11-228648
Patent Document 3: JP-A-11-240929
Patent Document 4: JP-A-11-240909
Patent Document 5: JP-A-2000-95791
Patent Document 6: WO2004-87775
Patent Document 7: JP-A-6-192500
Patent Document 8: JP-A-6-192506
Patent Document 9: JP-A-9-316145
Patent Document 10: JP-A-9-316147
Patent Document 11: JP-A-10-158351
Patent Document 12: WO95-27740
Patent Document 13: WO2005-23890
Patent Document 14: WO2005-23891
Patent Document 15: WO2005-23892
Patent Document 16: JP-A-10-226712
Patent Document 17: JP-A-2003-292700
Patent Document 18: JP-A-2004-002310
Patent Document 19: JP-A-2004-155739
Patent Document 20: JP-A-60-130604
Patent Document 21: JP-A-4-100808
Patent Document 22: JP-A-3-234709
Patent Document 23: JP-A-5-247128

Non-patent Document 1: Journal of the American Chemical Society 2001, vol. 123, p. 9555.
Non-patent Document 2: Polymer 2001, vol. 42, p. 9611.

SUMMARY OF INVENTION

Considering the above problems of conventional technologies, an object of the present invention is to provide a new transition metal compound constituting a catalyst for olefin polymerization in a metallocene type catalyst, that is, a new transition metal compound, which can form the metallocene type catalyst that has well-balanced reactivity between ethylene and a comonomer selected from α-olefins having 3 to 20 carbon atoms and produces an α-olefin polymer (hereinafter, may be referred to as CP) of a high molecular weight, and a catalyst for olefin polymerization containing this transition metal compound, and a method for producing a propylene/ethylene-α-olefin block copolymer using this catalyst for olefin polymerization.

Considering the rules of thumb from the standpoints such as symmetry of a transition metal compound derived from the basic skeleton, polymer forming mechanism at a catalyst active site, steric effect of a substituent of the transition metal compound and its effect on coordination of a formed polymer, regarding the ligand structure as a structure of the transition metal compound as a metallocene compound in a metallocene type polymerization catalyst, the present inventors have multifacetedly studied and carried out experimental search looking for means to improve the reactivity balance between ethylene and an α-olefin having 3 to 20 carbon atoms and thereby to improve the molecular weight, so as to solve such problems of the present invention.

In the course of study, when a transition metal compound having a specific steric structure is formed, the present inventors have recognized the fact that a transition metal compound having a specific steric structure gives well-balanced reactivity between ethylene and an α-olefin having 3 to 20 carbon atoms and shows thereby a catalytic function to give a high molecular weight, and have found, from the consideration of a model compound and the result of experimental demonstration, that a new metallocene metal complex that is very useful as a catalyst component and a metallocene catalyst for α-olefin polymerization can be realized, and completed the present invention.

That is, according to the first invention of the present invention, a transition metal compound represented by the following general formula is provided.

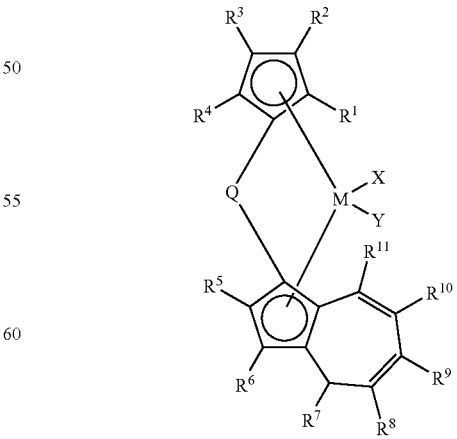

(wherein, $R^1$, $R^2$, $R^3$, $R^4$, $R^5$ and $R^6$ each independently are a hydrogen atom, a hydrocarbon group, a silicon-containing hydrocarbon group or a halogenated hydrocarbon group; however, any two or more of $R^1$, $R^2$, $R^3$ and $R^4$ are a substitute other than a hydrogen atom and any one or more of $R^1$, $R^2$, $R^3$ and $R^4$ are a hydrogen atom; further, adjacent $R^1$, $R^2$, $R^3$ and $R^4$ do not form a ring with each other; $R^7$ is a hydrocarbon group, a halogenated hydrocarbon group or a silicon-containing hydrocarbon group each having 6 or more carbon atoms; $R^8$, $R^9$, $R^{10}$ and $R^{11}$ each independently are a hydrogen atom, a hydrocarbon group, a silicon-containing hydrocarbon group or a halogenated hydrocarbon group; Q is a substituted silylene group or a substituted germylene group; X and Y each independently are a ligand that forms a σ-bond with M; and M is a transition metal of the groups 4 of the periodic table)

In addition, according to the second invention of the present invention, a transition metal compound characterized in that $R^1$ and $R^3$ are a substituent other than a hydrogen atom in the first invention is provided.

In addition, according to the third invention of the present invention, a catalyst for olefin polymerization characterized by containing the transition metal compound (A) according to the first or second invention is provided.

In addition, according to the fourth invention of the present invention, a catalyst for olefin polymerization characterized by further containing the following component (B) or both the component (B) and the component (C) in the third invention is provided.

Component (B): a compound selected from the group consisting of an organic aluminum oxy compound and an ionic compound or a Lewis acid that reacts with the component (A) and can change the component (A) to a cationic complex Component (C): fine particle support In addition, according to the fifth invention of the present invention, a catalyst for olefin polymerization characterized by further containing the following component (D) or both the component (D) and the component (E) in the third invention is provided.

Component (D): a compound selected from the group consisting of a ion-exchangeable layered compound and an inorganic silicate Component (E): an organoaluminum compound In addition, according to the sixth invention of the present invention, a method for producing an α-olefin polymer or copolymer characterized by using the catalyst for olefin polymerization according to any one invention of the third to fifth inventions is provided.

In addition, according to the seventh invention of the present invention, a method for producing a propylene/ethylene-α-olefin block copolymer characterized by being composed of the former-part step where a crystalline propylene polymer component is produced in the presence of the catalyst for olefin polymerization according to any one invention of the third to fifth inventions and the subsequent latter-part step where copolymer components of ethylene and at least one comonomer selected from α-olefins having 3 to 20 carbon atoms are produced by a gas phase polymerization in the presence of a crystalline propylene polymer component is provided.

In addition, according to the eighth invention of the present invention, a method for producing a propylene/ethylene-α-olefin block copolymer characterized in that a comonomer to be used in the latter-part step in the seventh invention is propylene is provided.

In addition, according to the ninth invention of the present invention, a method for producing a propylene/ethharacterisylene-α-olefin block copolymer characterized in that a comonomer to be used in the latter-part step in the seventh invention is selected from 1-butene, 1-hexene and 1-octene is provided.

As described above, the present invention relates to a new transition metal compound, a catalyst for olefin polymerization using the transition metal compound and a method for producing an olefin polymer or copolymer, and the preferable embodiments thereof include the following:

(1) in the above formula, the above transition metal compound characterized in that M is zirconium or hafnium, the catalyst for olefin polymerization containing this transition metal compound and the method for producing an olefin polymer or block copolymer using this catalyst for olefin polymerization (2) the transition metal compound of above (1) characterized in that the above formula is dichloro{1,1'-dimethylsilylene (2-methyl-4-phenylcyclopentadienyl)(2-methyl-4-phenyl-4H-azulenyl)}hafnium, or dichloro{1,1'-dimethylsilylene(2-methyl-4-phenylcyclopentadienyl)(2-methyl-4-(4-trimethylsilyl-3,5-dimethylphenyl)-4H-azulenyl)}hafnium, the catalyst for olefin polymerization containing this transition metal compound and the method for producing an olefin polymer or block copolymer using this catalyst for olefin polymerization.

According to the new transition metal compound of the present invention, the catalyst for olefin polymerization containing this transition metal compound and the method for producing a propylene/ethylene-α-olefin block copolymer using this catalyst for olefin polymerization, ethylene and a comonomer show well-balanced reactivity in copolymerization of ethylene and an α-olefin having 3 to 20 carbon atoms, which realizes polymerization by reasonably feeding a gas having a monomer ratio that is not substantially deviated from the content in the copolymer, further, a catalyst function to give a high molecular weight is shown at that time, a propylene/ethylene-α-olefin block copolymer excellent in impact resistance of which the ethylene-α-olefin copolymer has a higher molecular weight and a less content of low molecular weight components than conventional one can be stably and efficiently produced.

DETAILED DESCRIPTION OF THE INVENTION

The new transition metal compound of the present invention, the catalyst for olefin polymerization containing this transition metal compound and the method for producing a propylene/ethylene-α-olefin block copolymer using this catalyst for olefin polymerization will be described in detail below.

1. Transition Metal Compound to be Used for a Catalyst Component for Olefin Polymerization (1) Characteristics of the Transition Metal Compound A metallocene metal complex constituting the basic structure of the present invention is a new transition metal compound, having characteristics in a chemical and steric structure of a ligand in the metallocene catalyst and thus gives well-balanced reactivity between ethylene and an α-olefin having 3 to 20 carbon atoms and shows a catalyst function to give a high molecular weight.

Said metallocene complex is composed of a new transition metal compound of which the structure is represented by the following general formula and is used as a catalyst component of the catalyst for olefin polymerization in the present invention and constitutes a catalyst for α-olefin polymerization in combination with co-catalyst or the like.

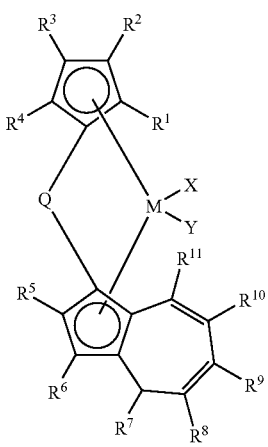

(wherein, $R^1$, $R^2$, $R^3$, $R^4$, $R^5$ and $R^6$ each independently are a hydrogen atom, a hydrocarbon group, a silicon-containing hydrocarbon group or a halogenated hydrocarbon group; however, any two or more of $R^1$, $R^2$, $R^3$ and $R^4$ are a substitute other than a hydrogen atom and any one or more of $R^1$, $R^2$, $R^3$ and $R^4$ are a hydrogen atom; further, adjacent $R^1$, $R^2$, $R^3$ and $R^4$ do not form a ring with each other; $R^7$ is a hydrocarbon group, a halogenated hydrocarbon group or a silicon-containing hydrocarbon group each having 6 or more carbon atoms; $R^8$, $R^9$, $R^{10}$ and $R^{11}$ each independently are a hydrogen atom, a hydrocarbon group, a silicon-containing hydrocarbon group or a halogenated hydrocarbon group; Q is a substituted silylene group or a substituted germylene group; X and Y each independently are a ligand that forms a σ-bond with M; and M is a transition metal of the group 4 of the periodic table)

The transition metal compound of the present invention has characteristics as a ligand of a complex in its chemical structure and specificity in the steric configuration of a substituent. A bulky substituent is arranged at 4-position on a cyclopentadienyl skeleton or a hydroazulenyl skeleton resulting in a specific and novel structure.

Further, the transition metal compound of the present invention includes two isomers (a: usually called anti isomer) and (b: usually called syn isomer) regarding a plane including M, X and Y in the standpoint of the relative position of a cyclopentadienyl skeleton and a hydroazulenyl skeleton via the bonding group Q.

In order to produce an α-olefin polymer of a high molecular weight, however, the above compound (a), that is, a compound, where two ligands facing each other across a plane including M, X and Y are not in the relation of a real image and a mirror image with respect to said plain, is preferably used from the standpoint of the function to regulate the growth direction of the polymer chain and the coordination direction of monomer.

Incidentally, each of the patent Documents and non-patent Documents described in BACKGROUND ART and still more other patent Documents etc. has been intensively examined on the new transition metal compound, which is composed of a cyclopentadienyl derivative and a hydroazulenyl derivative, disclosed in the present invention, then, patent Document 16 discloses part of the transition metal compounds similar to the present invention as an exemplified compound. This disclosure, however, gives nothing but exemplified description and does not describe at all that such a compound is synthesized and confirmed. Further, although patent Documents 17, 18 and 19 and other Documents disclose part of similar compounds, the new transition metal compound of the present invention is not found therein. Still more, there is no description at all that such a compound is actually synthesized and confirmed to have excellent properties for reactivity of ethylene and an α-olefin having 3 to 20 carbon atoms.

By using the transition metal compound of such present invention as a catalyst component for olefin polymerization, as demonstrated by comparison of examples and comparative examples described later, ethylene and a comonomer show well-balanced reactivity when ethylene and an α-olefin having 3 to 20 carbon atoms is copolymerized, as a result, which realizes polymerization by reasonably feeding a gas having a monomer ratio that is not substantially deviated from the content in the copolymer, and further, a catalyst function to give a high molecular weight is realized at that time, and a metallocene catalyst for α-olefin polymerization, wherein a propylene/ethylene-α-olefin block copolymer excellent in impact resistance of which the ethylene-α-olefin copolymer has a higher molecular weight and a less content of low molecular weight components than conventional one can be stably and efficiently produced, can be realized.

The reason is not necessarily clear, however, a transition metal compound represented by the chemical formula of the present invention is basically characterized by having a chemically, sterically and electronic environmentally peculiar structure along with a plurality of substituents on the cyclopentadienyl ring and sterically bulky substituents such as a branched alkyl group and an aromatic ring at 4-position of the hydroazulenyl ring. And the reason can be estimated as follows.

For such a transition metal compound having C2 symmetry (symmetry with a two-time rotation axis) as shown typically in the above patent Document 4 and the like, the two coordination sites have the same steric and electronic environment. In this case, the reactivity ratio between ethylene and a monomer for copolymerization such as an α-olefin having 3 to 20 carbon atoms is determined according to the environment of a coordination site that is determined by a ligand structure of the transition metal compound.

In contrast, for such a transition metal compound not having C2 symmetry as shown by the general chemical formula in the present invention, the two coordination sites have a different steric and electronic environment because of its low level of symmetry. In this case, the reactivity ratio between ethylene and a monomer for copolymerization differs in each coordination site. It is estimated that in such an environment of a coordination site, for example, the reactivity of ethylene becomes relatively large (in an extreme case, ethylene alone can selectively react) in one coordination site and the reactivity of a monomer for copolymerization becomes relatively large (in an extreme case, a monomer for copolymerization alone can selectively react) in another coordination site.

This shows that the reactivity in each coordination site can be freely changed by optionally changing a substituent in a transition metal compound. As a result, it will be possible to make the reactivity ratio, as catalyst performance, between ethylene and a monomer for copolymerization such as an α-olefin having 3 to 20 carbon atoms in a desired well-balanced range.

In addition, while it is well known by those of skill in the art that the molecular weight of a copolymer is determined by the balance between propagation reaction and termination reaction, it will be possible to control the termination reaction of polymerization by release of polymer chain caused by the steric effect of a substituent on each derivative in the case of a transition metal compound composed of a cyclopentadienyl derivative and a hydroazulenyl derivative as shown by the general formula. Particularly, it is considered that a substituent arranged on the cyclopentadienyl part has a large steric effect on the two coordination sites.

It is estimated that, in the case of small steric effect by a substituent in this part, a polymer chain is allowed to take a free conformation and a hydrogen atom at β-position is easily eliminated resulting in a low molecular weight and, in contrast, in the case of too large steric effect, the coordination site becomes narrow and a methyl group at β-position of a polymer chain is eliminated resulting again in a low molecular weight.

From the above consideration, it will be possible to improve a molecular weight by properly designing and controlling the steric effect of a substituent arranged on the cyclopentadienyl part.

(2) Structure of Transition Metal Compound

The transition metal compound of the present invention to form a metallocene complex in a metallocene catalyst is a new transition metal compound represented by the following general formula.

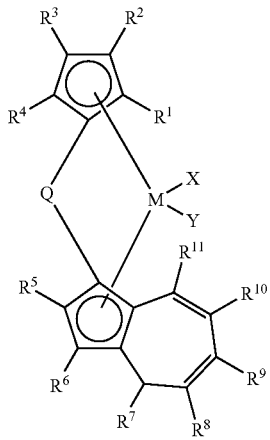

(wherein, $R^1$, $R^2$, $R^3$, $R^4$, $R^5$ and $R^6$ each independently are a hydrogen atom, a hydrocarbon group, a silicon-containing hydrocarbon group or a halogenated hydrocarbon group; however, any two or more of $R^1$, $R^2$, $R^3$ and $R^4$ are a substituent other than a hydrogen atom and any one or more of $R^1$, $R^2$, $R^3$ and $R^4$ are a hydrogen atom; further, adjacent $R^1$, $R^2$, $R^3$ and $R^4$ do not form a ring with each other; $R^7$ is a hydrocarbon group, a halogenated hydrocarbon group or a silicon-containing hydrocarbon group having 6 or more carbon atoms; $R^8$, $R^9$, $R^{10}$ and $R^{11}$ each independently are a hydrogen atom, a hydrocarbon group, a silicon-containing hydrocarbon group or a halogenated hydrocarbon group; Q is a substituted silylene group or a substituted germylene group; X and Y each independently are a ligand that forms a σ-bond with M; and M is a transition metal of the group 4 of the periodic table) Incidentally, a long-period type periodic table is used in the specification of the present application.

(3) Substituent of Transition Metal Compound

In the general formula, $R^1$, $R^2$, $R^3$, $R^4$, $R^5$ and $R^6$ each independently are a hydrogen atom, a hydrocarbon group, a silicon-containing hydrocarbon group or a halogenated hydrocarbon group.

Specific examples of the hydrocarbon group include an alkyl group such as methyl, ethyl, n-propyl, i-propyl, n-butyl, i-butyl, s-butyl, t-butyl, n-pentyl, n-hexyl, cyclopropyl, cyclopentyl and cyclohexyl; an alkenyl group such as vinyl, propenyl and cyclohexenyl; and an aryl group such as phenyl, tolyl, dimethylphenyl, ethylphenyl, trimethylphenyl, t-butylphenyl, 1-naphthyl, 2-naphthyl, acenaphthyl, phenanthryl and anthryl.

Specific examples of the silicon-containing hydrocarbon group preferably include a trialkylsilyl group such as trimethylsilyl, triethylsilyl and t-butyldimethylsilyl; and an alkylsilylalkyl group such as bis(trimethylsilyl)methyl.

Halogen atoms in the halogenated hydrocarbon group include a fluorine atom, a chlorine atom, a bromine atom and an iodine atom. The halogenated hydrocarbon group is, for example, in the case that the halogen atom is a fluorine atom, a compound where the fluorine atom substitutes at an optional position on the above hydrocarbon group.

Specific examples of the halogenated hydrocarbon include fluoromethyl, difluoromethyl, trifluoromethyl, chloromethyl, dichloromethyl, trichloromethyl, bromomethyl, dibromomethyl, tribromomethyl, iodomethyl, 2,2,2-trifluoroethyl, 2,2,1,1-tetrafluoroethyl, pentafluoroethyl, pentachloroethyl, pentafluoropropyl, nonafluorobutyl, trifluorovinyl, each fluorophenyl substituted at 2-, 3- and 4-position, each chlorophenyl substituted at 2-, 3- and 4-position, each bromophenyl substituted at 2-, 3- and 4-position, each difluorophenyl substituted at 2,4-, 2,5-, 2,6- and 3,5-positions, each dichlorophenyl substituted at 2,4-, 2,5-, 2,6- and 3,5-positions, 2,4,6-trifluorophenyl, 2,4,6-trichlorophenyl, pentafluorophenyl and pentachlorophenyl and the like.

Among these groups, $R^1$, $R^2$, $R^3$ and $R^4$ are preferably an alkyl group having 1 to 6 carbon atoms such as methyl, ethyl, propyl and butyl; or an aryl group having 1 to 12 carbon atoms such as a phenyl group and a naphthyl group.

However, any two or more of $R^1$, $R^2$, $R^3$ and $R^4$ are a substituent other than a hydrogen atom and any one or more of $R^1$, $R^2$, $R^3$ and $R^3$ are a hydrogen atom. Further, adjacent $R^1$, $R^3$, $R^3$ and $R^4$ do not form a ring with each other. Preferably, $R^1$ and $R^3$ are an atom other than hydrogen atom.

Preferably, $R^5$ is an alkyl group having 1 to 6 carbon atoms such as methyl, ethyl, propyl and butyl and $R^6$ is a hydrogen atom.

$R^7$ is a hydrocarbon group, a halogenated hydrocarbon group or a silicon-containing hydrocarbon group each having 6 or more carbon atoms and $R^8$, $R^9$, $R^{10}$ and $R^{11}$ each independently are a hydrogen atom, a hydrocarbon group, a silicon-containing hydrocarbon group or a halogenated hydrocarbon group.

Specific examples of the hydrocarbon group having 6 or more carbon atoms include an aryl group such as a phenyl, tolyl, dimethylphenyl, mesityl, ethylphenyl, diethylphenyl, triethylphenyl, i-propylphenyl, di-i-propylphenyl, tri-i-propylphenyl, n-butylphenyl, di-n-butylphenyl, tri-n-butylphenyl, t-butylphenyl, di-t-butylphenyl, tri-t-butylphenyl, biphenylyl, p-terphenyl, m-terphenyl, naphthyl, anthryl and phenanthryl.

Halogen atoms in the above halogenated hydrocarbon substituent having 6 or more carbon atoms include a fluorine atom, a chlorine atom, a bromine atom and an iodine atom. And the above halogenated hydrocarbon substituent is, for example, in the case that the halogen atom is a fluorine atom, a compound where the fluorine atom substitutes at an optional position on the above hydrocarbon group. Specific examples include a fluorodimethylphenyl, (fluoromethyl)methylphenyl, ethylfluorophenyl, diethylfluorophenyl, triethylfluorophenyl, fluoro-i-propylphenyl, fluoro-di-i-propylphenyl, (fluoro-i-propyl)i-propylphenyl, fluoro-tri-i-propylphenyl, n-butylfluorophenyl, di-n-butylfluorophenyl, (fluorobutyl) butylphenyl, tri-n-butylfluorophenyl, t-butylfluorophenyl, di-t-butylfluorophenyl, tri-t-butylfluorophenyl, fluorobiphenylyl, fluoro-p-terphenyl, fluoro-m-terphenyl, fluoronaphthyl, fluoroanthryl and fluorophenanthryl and the like.

Specific examples of the above silicon-containing hydrocarbon substituent having 6 or more carbon atoms include an aryl group substituted by a silyl group such as trimethylsilylphenyl, triethylsilylphenyl, isopropyldimethylsilylphenyl, t-butyldimethylsilylphenyl and phenyldimethylsilylphenyl.

$R^8$, $R^9$, $R^{10}$ and $R^{11}$ may be any group as long as they are not an especially bulky group and represent each a hydrogen atom, a hydrocarbon group, a halogenated hydrocarbon group or a silicon-containing hydrocarbon group.

Specific examples of the hydrocarbon group include an alkyl group such as methyl, ethyl, n-propyl, i-propyl and n-butyl; and an alkenyl group such as vinyl, propenyl and cyclohexenyl.

The halogenated hydrocarbon group is a compound having a halogen atom substitute at an optional position of the above hydrocarbon group. The halogen is preferably fluorine, chlorine or bromine, and more preferably fluorine or chlorine among them.

Specific examples of the halogenated hydrocarbon include fluoromethyl, difluoromethyl, trifluoromethyl, chloromethyl and dichloromethyl and the like.

Specific example of the silicon-containing hydrocarbon group include a trialkylsilyl group such as trimethylsilyl, triethylsilyl and t-butyldimethylsilyl; a trialkylsilylmethyl group such as trimethylsilylmethyl and triethylsilylmethyl; and a di(alkyl)(aryl)silylmethyl group such as dimethylphenylsilylmethyl and dimethyltolylsilylmethyl. $R^8$, $R^9$, $R^{10}$ and $R^{11}$ are preferably a hydrogen atom among these.

In the formula, Q is a bridging group that bonds two cyclopentadienyl rings and represents a substituted silylene group or a substituted germylene group.

Specific examples of Q include an alkylsilylene group such as methylsilylene, dimethylsilylene, diethylsilylene, di(n-propyl)silylene, di(i-propyl)silylene and di(cyclohexyl)silylene; an (alkyl)(aryl)silylene group such as methyl(phenyl)silylene and methyl(tolyl)silylene; an arylsilylene group such as diphenylsilylene; and further, a silacyclobutenyl group, a silacyclopropyl group, a silacyclohexyl group and a silafluorenyl group where a substituent on silicon has a ring structure. Substituents to be obtained by replacing a silicon atom of the above substituents with a germanium atom are also included.

X and Y are a ligand that forms a σ bond with M. X and Y are not particularly limited and preferably include a halogen atom, a hydrocarbon group having 1 to 20 carbon atoms and a substituted amino group or nitrogen-containing hydrocarbon group each having 1 to 20 carbon atoms. Among these, a chlorine atom, a methyl, an i-butyl, a phenyl, a benzyl, a dimethylamino and a diethylamino are particularly preferable.

M represents a transition metal of the group 4 of the periodic table and includes titanium, zirconium and hafnium, more preferably zirconium or hafnium.

(4) Synthesis of Transition Metal Compound

The transition metal compound of the present invention can be synthesized by an optional method with regard to a substituent and a binding style.

A typical synthesis route is shown by the following reaction scheme. For example, when substituents on the cyclopentadienyl part are $R^1$ and $R^3$ and substituents on the hydroazulenyl part are $R^5$ and $R^7$, the synthesis is carried out as follows.

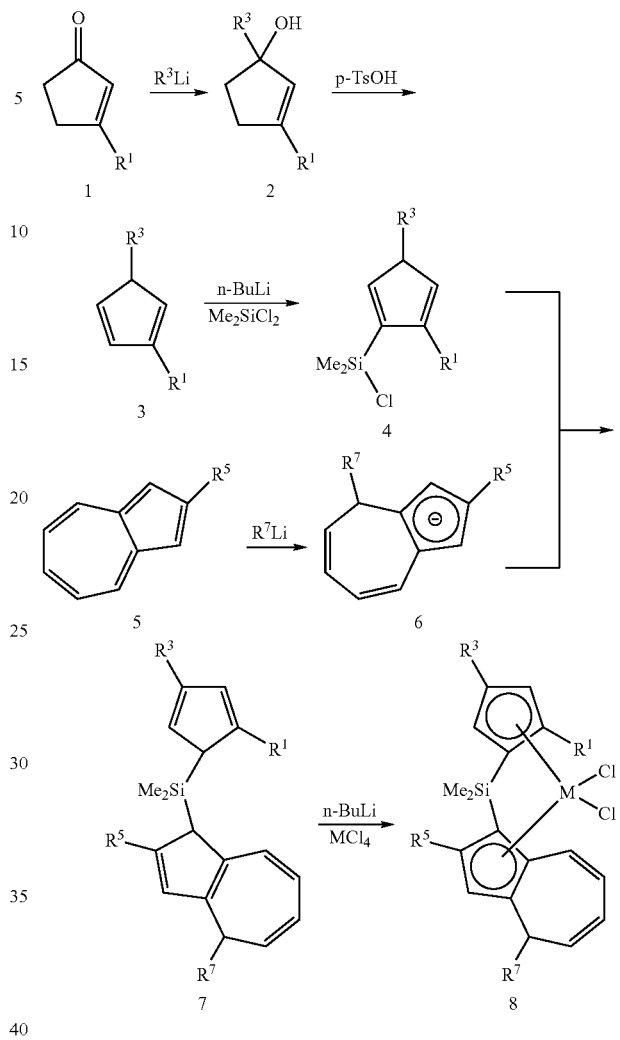

An alcohol (2) formed by reacting cyclopentanone (1) having an $R^1$ group with a lithium reagent having an $R^3$ group is dehydrated using p-toluenesulfonic acid or the like to obtain a cyclopentadienyl derivative (3) having the substituents at the desired positions. After removing a proton using n-butyllithium or the like, a cyclopentadienyl derivative (3) is reacted with dichlorodimethylsilane to obtain a chlorosilylated cyclopentadienyl derivative (4). In this case, the position substituted by a silicon atom is determined so as to take the most sterically vacant position of the substituents arranged on the cyclopentadienyl derivative. On the other hand, azulene (5) having an $R^5$ group is reacted with a lithium reagent having an $R^7$ group to obtain a compound (6) having the $R^7$ group added at 4-position of the azulenyl part. The obtained compound (6) is reacted with the chlorosilylated cyclopentadienyl derivative (4) to obtain a bridging ligand (7), which subsequently is deprotonated in a known manner and then reacted with zirconium tetrachloride or the like to obtain an objective transition metal compound (8).

It should be noted that, it is apparent that other transition metal compounds of the present invention can also be easily synthesized based on such the route of synthesis.

(5) Specific Examples of Transition Metal Compound

Preferable specific examples of the transition metal compound of the present invention are shown as follows. A hafnium dichloride is selected as a representative and the name of the compound having the following structural formula is exemplified.

The compound having this structural formula is called dichloro{1,1'-dimethylsilylene(2,3,5-trimethylcyclopentadienyl)(2-methyl-4-phenyl-4H-azulenyl)}hafnium.

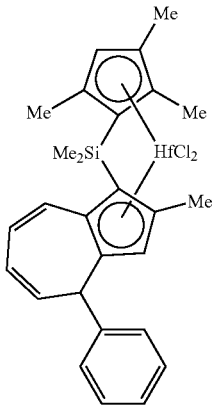

Incidentally, since a new transition metal compound is the main element of the present invention, it is basically necessary to exemplify many transition metal compounds as the example. Exemplification of the transition metal compounds, however, is limited to the main representative examples avoiding complex description in order to make the specification simple. Therefore, besides the transition metal compounds given below, other transition metal compounds are also included in the scope described in the claims of the present application. For example, it should be considered that the compounds containing titanium or zirconium instead of hafnium or the compounds containing other X and Y instead of a dichloride are also exemplified in the following specific examples.

Incidentally, compounds having similarity are arranged in each paragraph in the following exemplifications.
(1) dichloro{1,1'-dimethylsilylene(2,3-dimethylcyclopentadienyl)(2-methyl-4-phenyl-4H-azulenyl)}hafnium
(2) dichloro{1,1'-dimethylsilylene(3,4-dimethylcyclopentadienyl)(2-methyl-4-phenyl-4H-azulenyl)}hafnium
(3) dichloro{1,1'-dimethylsilylene(2,5-dimethylcyclopentadienyl)(2-methyl-4-phenyl-4H-azulenyl)}hafnium
(4) dichloro{1,1'-dimethylsilylene(2,3-di-t-butylcyclopentadienyl)(2-methyl-4-phenyl-4H-azulenyl)}hafnium
(5) dichloro{1,1'-dimethylsilylene(3,4-di-t-butylcyclopentadienyl)(2-methyl-4-phenyl-4H-azulenyl)}hafnium
(6) dichloro{1,1'-dimethylsilylene(2,5-di-t-butylcyclopentadienyl)(2-methyl-4-phenyl-4H-azulenyl)}hafnium
(7) dichloro{1,1'-dimethylsilylene(2,3-diphenylcyclopentadienyl)(2-methyl-4-phenyl-4H-azulenyl)}hafnium
(8) dichloro{1,1'-dimethylsilylene(3,4-diphenylcyclopentadienyl)(2-methyl-4-phenyl-4H-azulenyl)}hafnium
(9) dichloro{1,1'-dimethylsilylene(2,5-diphenylcyclopentadienyl)(2-methyl-4-phenyl-4H-azulenyl)}hafnium
(10) dichloro{1,1'-dimethylsilylene(2-methyl-4-ethylcyclopentadienyl)(2-methyl-4-phenyl-4H-azulenyl)}hafnium
(11) dichloro{1,1'-dimethylsilylene(2-ethyl-4-methylcyclopentadienyl)(2-methyl-4-phenyl-4H-azulenyl)}hafnium
(12) dichloro{1,1'-dimethylsilylene(4-t-butyl-2-methylcyclopentadienyl)(2-methyl-4-phenyl-4H-azulenyl)}hafnium
(13) dichloro{1,1'-dimethylsilylene(2-methyl-4-phenylcyclopentadienyl)(2-methyl-4-phenyl-4H-azulenyl)}hafnium
(14) dichloro{1,1'-dimethylsilylene(2,3,4-trimethylcyclopentadienyl)(2-methyl-4-phenyl-4H-azulenyl)}hafnium
(15) dichloro{1,1'-dimethylsilylene(2,4,5-trimethylcyclopentadienyl)(2-methyl-4-phenyl-4H-azulenyl)}hafnium
(16) dichloro{1,1'-dimethylsilylene(2,3-dimethyl-4-phenylcyclopentadienyl)(2-methyl-4-phenyl-4H-azulenyl)}hafnium
(17) dichloro{1,1'-dimethylsilylene(2,3-dimethyl-5-phenylcyclopentadienyl)(2-methyl-4-phenyl-4H-azulenyl)}hafnium
(18) dichloro{1,1'-dimethylsilylene(2-methyl-4-phenylcyclopentadienyl)(2-ethyl-4-phenyl-4H-azulenyl)}hafnium
(19) dichloro{1,1'-dimethylsilylene(2,4,5-trimethylcyclopentadienyl)(2-ethyl-4-phenyl-4H-azulenyl)}hafnium
(20) dichloro{1,1'-dimethylsilylene(2-methyl-4-phenylcyclopentadienyl)(4-phenyl-2-i-propyl-4H-azulenyl)}hafnium
(21) dichloro{1,1'-dimethylsilylene(2,4,5-trimethylcyclopentadienyl)(4-phenyl-2-i-propyl-4H-azulenyl)}hafnium
(22) dichloro{1,1'-dimethylsilylene(2-methyl-4-phenylcyclopentadienyl)(4-(4-chlorophenyl)-2-methyl-4H-azulenyl)}hafnium
(23) dichloro{1,1'-dimethylsilylene(2,4,5-trimethylcyclopentadienyl)(4-(4-chlorophenyl)-2-methyl-4H-azulenyl)}hafnium
(24) dichloro{1,1'-dimethylsilylene(2-methyl-4-phenylcyclopentadienyl)(2-methyl-4-(3-methylphenyl)-4H-azulenyl)}hafnium
(25) dichloro{1,1'-dimethylsilylene(2,4,5-trimethylcyclopentadienyl)(2-methyl-4-(3-methylphenyl)-4H-azulenyl)} hafnium
(26) dichloro{1,1'-dimethylsilylene(2-methyl-4-phenylcyclopentadienyl)(4-(4-t-butylphenyl)-2-methyl-4H-azulenyl)}hafnium
(27) dichloro{1,1'-dimethylsilylene(2,4,5-trimethylcyclopentadienyl)(4-(4-t-butylphenyl)-2-methyl-4H-azulenyl)} hafnium
(28) dichloro{1,1'-dimethylsilylene(2-methyl-4-phenylcyclopentadienyl)(2-methyl-4-(2-naphthyl)-4H-azulenyl)}hafnium
(29) dichloro{1,1'-dimethylsilylene(2,4,5-trimethylcyclopentadienyl)(2-methyl-4-(2-naphthyl)-4H-azulenyl)}hafnium
(30) dichloro{1,1'-methylphenylsilylene(2-methyl-4-phenylcyclopentadienyl)(2-methyl-4-phenyl-4H-azulenyl)}hafnium
(31) dichloro{1,1'-silacyclobutenyl(2,4,5-trimethylcyclopentadienyl)(2-methyl-4-phenyl-4H-azulenyl)}hafnium
(32) dichloro{1,1'-silacyclopropenyl(2,4,5-trimethylcyclopentadienyl)(2-methyl-4-phenyl-4H-azulenyl)}hafnium
(33) dichloro{1,1'-silafluorenyl(2,4,5-trimethylcyclopentadienyl)(2-methyl-4-phenyl-4H-azulenyl)}hafnium
(34) dichloro{1,1'-methylphenylgermylene(2-methyl-4-phenylcyclopentadienyl)(2-methyl-4-phenyl-4H-azulenyl)}hafnium
(35) dichloro{1,1'-germacyclobutenyl(2,4,5-trimethylcyclopentadienyl)(2-methyl-4-phenyl-4H-azulenyl)}hafnium
(36) dichloro{1,1'-germacyclopropenyl(2,4,5-trimethylcyclopentadienyl)(2-methyl-4-phenyl-4H-azulenyl)} hafnium
(37) dichloro{1,1'-germafluorenyl(2,4,5-trimethylcyclopentadienyl)(2-methyl-4-phenyl-4H-azulenyl)}hafnium As described above, in a series of above compounds, compounds to be obtained by replacing one or both of two chlorine atoms that correspond to X and Y of the general formula with a fluorine atom, a bromine atom, an iodine atom, a methyl group, a phenyl group, a benzyl group, a dimethylamino group, an diethylamino group or the like can also be exemplified. In addition, it should be considered that compounds to be obtained by replacing hafnium of the core metal (M) of compounds exemplified in the above with titanium or zirconium are also exemplified.

Incidentally, it is generally known in the technical field of a catalyst for olefin polymerization that the kind of the metal in a transition metal compound that composes a catalyst has much effect on the catalyst function. It is not theoretically assured that two catalysts that differ only the kind of metal in a transition metal compound have an equivalent catalytic action. However, it has been experimentally confirmed and is well known by those having skill in the art that metallocene catalysts each having zirconium, titanium and hafnium of the group 4 of the periodic table exhibit almost the equivalent catalytic action (see Patent Documents 20 and 21).

It is apparent, therefore, that the above illustration of metallocene compounds in the present specification is reasonable rather than merely enumeration.

2. Catalyst for Olefin Polymerization

The transition metal compound of the present invention constitutes a catalyst component for olefin polymerization, which can be used in a catalyst for olefin polymerization. For example, a catalyst for olefin polymerization to be described as follows that contains the above catalyst component for olefin polymerization as the component (A) is preferably used.

(1) Catalyst (i) for Olefin Polymerization

The catalyst (i) for olefin polymerization is composed of the component (A) and the component (B). The term "composed of" is not intended to exclude other components besides these components and the system may further contain, for example, a support (C) and an organoaluminum compound.

Specific examples of the component (B) include following (B-1) to (B-3).
(B-1) an aluminum oxy compound
(B-2) an ionic compound or a Lewis acid that reacts with the component (A) and can change the component (A) to a cationic complex
(B-3) a solid acid In the aluminum oxy compound (B-1), aluminum oxy compound is known to be able to activate a metallocene complex and specifically includes the compounds represented by following general formulae (I) to (III).

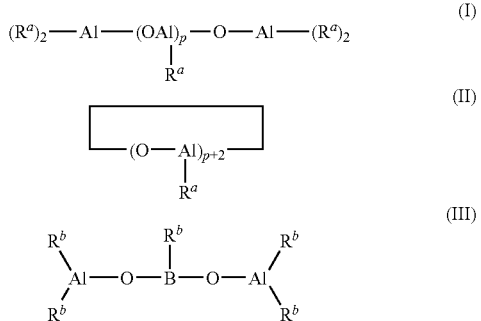

In each general formula above, $R^a$ is a hydrogen atom or a hydrocarbon group, a hydrocarbon having preferably 1 to 10 carbon atoms, particularly preferably 1 to 6 carbon atoms. Each of a plurality of $R^a$ may be the same or different. In addition, p is an integer of 0 to 40, preferably 2 to 30. Among the above general formulae, the compounds represented by general formulae (I) and (II) are also called aluminoxanes. Among these, methylaluminoxane or methylisobutylaluminoxane is preferable. Several kinds of the above aluminoxanes can be used together in or across each group. And the above aluminoxanes can be prepared under various known conditions.

The compound represented by general formula (III) can be obtained by reacting one kind of trialkylaluminum or two or more kinds of trialkylaluminum and an alkylboronic acid represented by the general formula $R^b B(OH)_2$ at a molar ratio of 10:1 to 1:1. In the general formula, $R^b$ is a hydrocarbon group having 1 to 10 carbon atoms, preferably 1 to 6 carbon atoms.

The compound (B-2) is an ionic compound or a Lewis acid that can react with the component (A) and change the component (A) to a cation. Such an ionic compound includes a complex of a cation such as a carbonium cation and an aluminum cation and an organic boron compound such as triphenylboron, tris(3,5-difluorophenyl)boron and tris(pentafluorophenyl)boron.

As examples of the above Lewis acid, various organic boron compounds, for example, tris(pentafluorophenyl)boron and the like is exemplified. Or halogenated metal compounds such as aluminum chloride and magnesium chloride are exemplified.

Incidentally, some of the above Lewis acids may be classified as an ionic compound that can react with the component (A) and change the component (A) to a cation.

Metallocene catalysts using the above-described non-coordinate boron compound are exemplified in Patent Document 22, Patent Document 23 and the like.

The solid acid (B-3) includes alumina, silica, silica-alumina, silica-magnesia and the like.

The support (C) as an optional component in the catalyst for olefin polymerization (i) of the present invention is composed of an inorganic or organic compounds and a particulate support having a particle diameter of usually 5 μm to 5 mm, preferably 10 μm to 2 mm.

The inorganic support includes, for example, an oxide such as $SiO_2$, $Al_2O_3$, MgO, ZrO, $TiO_2$, $B_2O_3$ and ZnO; a composite oxide such as $SiO_2$—MgO, $SiO_2$—$Al_2O_3$, $SiO_2$—$TiO_2$, $SiO_2$—$Cr_2O_3$ and $SiO_2$—$Al_2O_3$—MgO.

The organic support includes a particulate support of a porous polymer composed of, for example, a (co)polymer of an α-olefin having 2 to 14 carbon atoms such as ethylene, propylene, 1-butene, 4-methyl-1-pentene and a (co)polymer of an unsaturated aromatic hydrocarbon such as styrene and divinylbenzene.

These particles have a specific surface area of usually 20 to 1,000 m²/g, preferably 50 to 700 m²/g and a pore volume of usually 0.1 cm³/g or more, preferably 0.3 cm³/g or more and more preferably 0.8 cm³/g or more.

The catalyst (i) for olefin polymerization of the present invention may contain, as an optional component other than a particulate support, for example, a compound containing active hydrogen such as $H_2O$, methanol, ethanol and butanol; an electron donor compound such as an ether, an ester and an amine; phenyl borate, dimethylmethoxyaluminum, phenylphosphite; or an alkoxy-containing compound such as tetraethoxysilane and diphenyldimethoxysilane.

Optional components other than the above components include a tri-lower alkyl aluminium such as trimethylaluminum, triethylaluminum and triisobutylaluminum; a halogen-containing alkylaluminum such as diethylaluminum chloride, diisobutylaluminum chloride and methylaluminum sesquichloride; an alkylaluminum hydride such as diethylaluminum hydride; an alkoxy-containing alkylaluminum such as diethylaluminum ethoxide and dimethylaluminum butoxide; and an aryloxy-containing alkylaluminum such as diethylaluminum phenoxide.

An aluminum oxy compound and an ionic compound or a Lewis acid that can react with the component (A) and change the component (A) to a cation are each used alone as the component (B) in the catalyst for olefin polymerization (i) of the present invention. In addition, these three components may be used in combination as appropriate. Even though one or two or more of the above lower alkyl aluminium, halogen-containing alkylaluminum, alkylaluminum hydride, alkoxy-containing alkylaluminum and aryloxy-containing alkylaluminum are an optional component, they are preferably contained in the catalyst for olefin polymerization (i) along with an aluminum oxy compound, an ionic compound or a Lewis acid.

The catalyst for olefin polymerization (i) of the present invention can be prepared by contacting the component (A) and the component (B) in the presence or absence of a monomer to be polymerized inside or outside a polymerization reactor. That is, the component (A) and the component (B) and the component (C) as needed may be introduced separately into a polymerization reactor or the component (A) and the component (B) may be contacted in advance and then introduced into a polymerization reactor. In addition, a mixture of the component (A) and the component (B) may be impregnated in the component (C) and then introduced into a polymerization reactor.

The contact of each component above may be conducted in an inactive hydrocarbon solvent such as pentane, hexane, heptane, toluene and xylene under an atmosphere of an inert gas such as nitrogen. The contact temperature is preferably in the range from −20° C. to the boiling point of a solvent, particularly preferably in the range from room temperature to the boiling point of a solvent. The catalyst thus prepared may be used without washing after preparation or may be used after washing. Further, the catalyst may be added with a new component as needed after preparation.

(2) Catalyst (ii) for Olefin Polymerization

The catalyst (ii) for olefin polymerization is composed of the component (A), the component (D) and the component (E) to be used as needed. The term "composed of" is intended to have the similar meaning to one described in the catalyst (i) for olefin polymerization.

The component (D) is selected from the group consisting of an ion-exchangeable layered compound and an inorganic silicate. The component (E) is an organoaluminum compound.

Among the components (D), the ion-exchangeable layered compound occupies the major part of a clay mineral and is preferably an ion-exchangeable phyllosilicate.

The ion-exchangeable phyllosilicate (hereinafter, may be abbreviated as "silicate" for simplicity) is a silicate which has a crystalline structure that each plane constituted by an ionic bond or the like is stacked in parallel by the bonding strength, and in which the contained ion is exchangeable. Since most of silicates are produced mainly as the major component of natural clay minerals, they often contain foreign matters (quartz, cristobalite and the like) other than ion-exchangeable phyllosilicates. These foreign matters may be contained. Various known silicates may be used. Typical examples of silicates specifically include the following phyllosilicates, which are described in "Clay Mineralogy" written by Shiramizu Haruo, published by Asakura Shoten (1995).

2:1-Type Minerals

A smectite group such as montmorillonite, sauconite, beidellite, nontronite, saponite, hectorite and stevensite; a vermiculite group such as vermiculite; a mica group such as mica, illite, sericite and glauconite; a pyrophylite-talk group such as pyrophylite and talk; a chlorite group such as magnesium chlorite 2:1-Ribbon-Type Minerals Sepiolite, Palygorskite and the Like The silicate to be used as a raw material in the present invention may be a phyllosilicate constituted by the above mixed layers. In the present invention, the main component silicate is preferably a silicate having a 2:1 type structure, more preferably a smectite group and particularly preferably montmorillonite. A natural silicate or a silicate procured as an industrial raw material to be used in the present invention can be used as it is, without being particularly treated, but is preferably subjected to chemical treatment. The chemical treatment includes specifically acid treatment, alkali treatment, salts treatment, organic compound treatment and the like. The treatment may be combined with each other. In the present invention, the treatment conditions are not particularly limited and known conditions may be used.

In addition, since these ion-exchangeable phyllosilicates usually contain adsorbed water and interlayer water, they are preferably subjected to heat-dehydration treatment under inert-gas flow before use.

In the catalyst (ii) for olefin polymerization of the present invention, one example of organoaluminum compounds as the optional component (E) is represented by the following general formula.

$$AlR_aX_{3-a}$$

In the above general formula, R represents a hydrocarbon group having 1 to 20 carbon atoms; X represents hydrogen, a halogen, an alkoxy group or a siloxy group; and (a) represents a number of more than 0 and 3 or less. Specific examples of the organoaluminum compounds represented by the above general formula include a trialkylaluminum such as trimethylaluminum, triethylaluminum, tripropylaluminum and triisobutylaluminum; and a halogen- or alkoxy-containing alkylaluminum such as diethylaluminum monochloride and diethylaluminum monomethoxide. Among these, a trialkylaluminum is preferable.

In the catalyst (ii) for olefin polymerization of the present invention, aluminoxanes such as methylaluminoxane may be used as the component (E) besides the organoaluminum compounds represented by the above general formula. In addition, the above organoaluminum compounds and the aluminoxanes may be used together.

The catalyst (ii) for olefin polymerization of the present invention can be prepared similarly to the catalyst (i) for olefin polymerization. In this preparation, the method for contacting the component (A), the component (D) and the optional component (E) is not particularly limited, but the following methods may be exemplified as examples.

(1) method of contacting the component (A) and the component (D)
(2) method of contacting the component (A) and the component (D) followed by adding the optional component (E)
(3) method of contacting the component (A) and the optional component (E) followed by adding the component (D)
(4) method of contacting the component (D) and the optional component (E) followed by adding the component (A)
(5) method of contacting each component (A), (D) and (E) simultaneously Incidentally, this contact may be conducted not only in catalyst preparation but also in prepolymerization with an olefin or polymerization of an olefin. During or after the above contact of each component, a polymer such as polyethylene and polypropylene and a solid inorganic oxide such as silica and alumina may be present or contacted.

In addition, the above contact of each component may be conducted in an inactive hydrocarbon solvent such as pentane, hexane, heptane, toluene and xylene under an atmosphere of an inert gas such as nitrogen. The contact temperature is preferably in the range from −20° C. to the boiling point of a solvent, particularly preferably in the range from room temperature to the boiling point of a solvent.

(3) Amount of Use of Catalyst Component and so on

The amount of use of the component (a) and the component (B) or the component (D) is at an optimum ratio for respective combinations.

When the component (B) is an aluminum oxy compound, the optimum molar ratio of Al/transition metal is in the range of usually from 100 or more to 100,000 or less, further from 100 or more to 20,000 or less, and particularly from 100 or more to 10,000 or less. On the other hand, when the component (B) is an ionic compound or a Lewis acid, the molar ratio to a transition metal is 0.1 to 1,000, preferably 0.5 to 100 and more preferably 1 to 50.

When the component (B) is a solid acid, or when the component (D) is an ion-exchangeable layered compound, the transition metal complex is in the range from 0.001 to 10 mmol, preferably from 0.001 to 1 mmol per gram of the component.

These ratios of use show a usual ratio example and it is natural that the present invention is not limited to the above range of ratio of use, as long as the catalyst meets the object of the invention.

A catalyst for producing a polyolefin composed of a transition metal complex and co-catalyst may be subjected to prepolymerization treatment where a small amount of an olefin such as ethylene, propylene, 1-butene, 1-hexene, 1-octene, 4-methyl-1-pentene, 3-methyl-1-butene, a vinylcycloalkane and styrene is preliminarily polymerized after supported by a support as needed, before being used as a catalyst for an olefin polymerization (main polymerization). The method for prepolymerization may be a known method.

3. Method for Producing a Polymer or Copolymer of an α-Olefin and Method for Producing a Propylene/Ethylene-α-Olefin Block Copolymer The method for producing a propylene/ethylene-α-olefin block copolymer of the present invention is composed of a former-part step where a crystalline propylene polymer component (PP) is produced and a subsequent latter-part step where a copolymer component (CP) of ethylene and at least one comonomer selected from α-olefins having 3 to 20 carbon atoms is produced.

Any polymerization method of a slurry polymerization method, a bulk polymerization method and a gas-phase polymerization method may be used in the former-part step. For example, the slurry polymerization method using an inactive solvent can be carried out in an inactive hydrocarbon such as n-butane, isobutene, n-pentane, isopentane, hexane, heptane, octane, cyclohexane, benzene, toluene and xylene, or in a liquid monomer, whereas the bulk polymerization method includes a method of using a monomer to be polymerized as a solvent.

The gas-phase polymerization is used in the latter-part step, because an ethylene-α-olefin copolymer component is a rubber component which does not desirably elute in a solvent.

In addition, any polymerization system of a batch system and a continuous system may be used in the former-part step and the latter-part step. Two-stage polymerization composed of a former-part step and a latter-part step is carried out in the present invention, but each stage may be further divided as needed. Especially, the method for producing many kinds of rubber components by dividing the latter-part step into two or more stages is one method for improving properties.

(1) Production of Propylene Polymer Component (PP)

In a polymerization step of the former-part step, a crystalline propylene polymer component (PP) is produced using a metallocene catalyst, preferably a catalyst containing above-described component (A), more preferably a catalyst composed of above-described components (A), (B) or (D) and components (C) or (E) as needed. That is, a polymer of propylene alone (propylene homopolymer) or a copolymer of propylene and an α-olefin (propylene-α-olefin copolymer) is formed in a single stage or multistage in this step so as to occupy the amount corresponding to 20 to 99% by weight, preferably 30 to 90% by weight of the total amount of polymerization (the whole of a propylene/ethylene-α-olefin block copolymer). Here, the α-olefin includes ethylene and an α-olefin having 4 to 20 carbon atoms such as 1-butene, 1-hexene, 4-methyl-pentene-1,1-octene and 1-decene excluding propylene. Ethylene is most preferable among these. The amount of use of an α-olefin is 10% by weight or less, preferably 5% by weight or less relative to the whole monomer (total of propylene and α-olefin).

The polymerization temperature in the polymerization step of the former-part step is about 30 to 120° C., preferably about 50 to 90° C. The polymerization pressure is 0.1 to 6 MPa, preferably 0.1 to 4 MPa. In addition, a molecular weight (MFR) modifier is preferably used to obtain suitable fluidity of a polymer and hydrogen is preferable as a modifier. The MFR (test conditions: 230° C., 2.16 kg load) is 0.1 to 3,000 g/10 minutes, preferably 0.5 to 2,000 g/10 minutes and more preferably 0.5 to 1,000 g/10 minutes depending on a use of the final polymer.

(2) Production of Ethylene-α-Olefin Copolymer Component (CP)

The polymerization step of the latter-part step of the present invention is necessary to be carried out with a gas-phase polymerization because an ethylene-α-olefin copolymer component produced in this step is a rubber component which does not desirably elute in a solvent. As the gas-phase polymerization process, any known gas-phase polymerization process may be used, but a mechanically stirred vertical or horizontal gas-phase polymerization process is preferable.

In the latter-part step of the present invention, an ethylene-α-olefin copolymer having a polymerization ratio (molar ratio) of ethylene and an α-olefin of 95/5 to 50/50, preferably 90/10 to 70/30 is produced.

Here, the α-olefin includes an α-olefin having 3 to 20 carbon atoms, for example, such as propylene, 1-butene, 1-hexene, 4-methyl-pentene-1,1-octene and 1-decene. Propylene, 1-butene and 1-hexene are most preferable among these. The copolymer may further contain a different α-olefin or a diene family monomer other than the comonomer as a third component. In this case, the content of the third component is preferably 20% by weight or less.

In addition, in the latter-part step, the amount corresponding to 1 to 80% by weight, preferably 10 to 70% by weight of the total amount of polymerization (the whole of a propylene/ethylene-α-olefin block copolymer) is formed.

The polymerization temperature in the polymerization step of the latter-part step is about 30 to 120° C., preferably about 50 to 80° C. The polymerization pressure is 0.1 to 5 MPa, preferably 0.5 to 4 MPa. Too high polymerization pressure is known to cause a supercritical state, which is not involved in the gas-phase polymerization of the present invention.

A molecular weight modifier is preferably used in polymerization to obtain suitable fluidity of a polymer and hydrogen is preferable as a modifier.

The weight average molecular weight of an ethylene-α-olefin copolymer ranges from 10,000 to 5,000,000, preferably from 50,000 to 3,000,000, more preferably from 100,000 to 1,000,000 and most preferably from 400,000 to 800,000. The weight average molecular weight of an ethylene-α-olefin copolymer as close as possible to the weight average molecular weight of a polymer produced in the former-part step is effective in suppressing gel formation during molding and decreasing a linear expansion coefficient, although it depends on a use of the final polymer. Considering the properties of a polymer, it is desirable to suppress to the utmost the formation of a low molecular weight component in rubber that is said to cause sticking. Specifically, components having a molecular weight of 5,000 or less in rubber are preferably 0.8% by weight or less relative to the whole rubber. For this purpose, it is necessary to prevent polymerization reaction from proceeding under the condition different from that of the polymerization step of the latter-part step by taking such polymerization conditions not to decrease an average molecular weight of the rubber, or discharging remaining monomers or deactivating catalysts swiftly after polymerization. Incidentally, the amount of a low molecular weight component in a rubber means here an amount of a component having a molecular weight of 5,000 or less in the eluted components at 40° C. or less in the measurement with a CFC analyzer to be described later.

4. Propylene/Ethylene-α-Olefin Block Copolymer

By the above production method, an ethylene-α-olefin copolymer component (CP) can be produced so as to be 1 to 80% by weight, preferably 10 to 70% by weight relative to the total amount of polymerization (the whole of a propylene/ethylene-α-olefin block copolymer). In addition, it is possible to make the ethylene content in rubber (CP) 99 to 50% by weight, preferably 95 to 60% by weight. Further, it is possible to make the intrinsic viscosity $[\eta]_{cp}$ of a rubber (CP) portion 1 to 10, preferably 3 to 10.

It is possible to make the melting point (Tm) of a crystalline propylene polymer component (PP) 120 to 165° C., preferably 150 to 165° C.

EXAMPLES

In order to explain the present invention more specifically and clearly, the present invention will be described by contrasting the examples with the comparative examples to prove the constituent features of the present invention to be reasonable and significant.

Incidentally, in the following various examples, the catalyst synthesis step and the polymerization step are all conducted under an atmosphere of purified nitrogen using a solvent dehydrated with MS-4A (molecular sieve) followed by bubbling with purified nitrogen for deaeration. In addition, methods for measurement and evaluation in the present invention are as follows.

Next, the present invention will be described in further detail with reference to examples. The present invention, however, is by no means limited by these examples.

Methods for measuring the polymer properties evaluated in the examples are shown below.

(1) Measurement of MFR:

To 6 g of a polymer, 6 g of a solution (0.6% by weight) of a thermal stabilizer (BHT) in acetone was added. The above polymer was then dried, filled in a melt indexer (230° C.) and left for standing for 5 minutes under a load of 2.16 kg. Subsequently, the extruding rate of the polymer was measured and converted to the rate per 10 minutes to obtain MFR (unit is g/10 minutes).

(2) Measurement of Melting Point (Tm):

After heating a polymer from 20 to 200° C. followed by cooling to 20° C. at a rate of 10° C./minute once, the melting point was measured in the second heating at a rate of 10° C./minute with DSC (made by Seiko Instruments Inc., DCS6200 model).

(3) Cross Fractionation (Hereinafter, Referred to as CFC):

The content of a copolymer component (a rubber component, hereinafter, referred to as CP) in a propylene/ethylene-α-olefin block copolymer obtained by using a catalyst of the present invention and the polymerization ratio of an α-olefin in the CP were determined by the following method.

Incidentally, the following examples are for the case that propylene is used as an α-olefin in a CP (that is, assumed to be an ethylene-propylene copolymer) and the similar method to the following examples shall be used for the case that 1-butene or the like is used as an α-olefin.

(3-1) Analyzers to be Used (i) Cross fractionation:

CFC made by Dia Instruments Co., ltd. T-100

(ii) Fourier transform infrared spectroscopy:

FT-IR made by PerkinElmer, Inc. 1760X

A fixed-wavelength type infrared spectrophotometer installed as a detector of CFC is removed and Ft-IR is connected and used as a detector instead. A transfer line of a liquid eluted from CFC has a length of 1 m between the outlet of CFC and FT-IR and is kept at 140° C. during measurement. A flow cell attached to FT-IR has an optical pass length of 1 mm and an optical pass width of 5 mmΦ in diameter and is kept at 140° C. during measurement.

(iii) Gel permeation chromatography (GPC)

Three GPC columns (made by Showa Denko K.K. AD806MS) are connected in series to the latter-part step of CFC.

(3-2) Measurement Conditions of CFC (i) Solvent: orthodichlorobenzene (ODCB)

(ii) Concentration of sample: 4 mg/mL (iii) Injected amount: 0.4 mL (iv) Crystallization: cooling from 140° C. to 40° C. in about 40 minutes (v) Fractionation method: The fractionation temperature in heating, elution and fractionation is set at 40, 100 and 140° C. and a sample is divided into three fractions. Incidentally, the elution ratios (unit: % by weight) of the components eluted at 40° C. or less (Fraction 1), the components eluted between 40° C. and 100° C. (Fraction 2) and the components eluted between 100° C. and 140° C. (Fraction 3) are defined as W40, W100 and W140 respectively. W40+W100+W140=100. In addition, Each fraction is automatically sent as it is to the FT-IR analyzer.

(vi) Flow rate of a solvent in elution: 1 mL/minute (3-3) Measurement Conditions of FT-IR After a sample solution begins to be eluted from GPC at the latter-part step of CFC, FT-IR measurement is conducted under the following conditions for each of the above fractions 1 to 3 to obtain GPC-IR data.

(i) Detector: MCT (ii) Resolution: 8 cm$^{-1}$ (iii) Measurement interval: 0.2 minutes (12 seconds)

(iv) Integration frequency in one measurement: 15 times (3-4) Aftertreatment and Analysis of Measurement Results The eluted amount and the molecular weight distribution of the component eluted at each temperature are determined using absorbance at 2,945 cm$^{-1}$ obtained by FT-IR as a chromatogram. The eluted amount is normalized so that the sum of the eluted amount of each eluted component becomes 100%. The working curve prepared in advance using standard polystyrene is used to convert retention volume to molecular weight. Every standard polystyrene used is products of Tosoh Corporation having each the following trade name.

F380, F288, F128, F80, F40, F20, F10, F4, F1, A5000, A2500 and A1000

0.4 mL of each solution obtained by dissolving the standard polystyrene in ODCB (containing 0.5 mg/mL BHT) so as to be 0.5 mg/mL is injected to draw a calibration curve. A cubic equation obtained by approximation with the least-squares method is used to draw the calibration curve. A general calibration curve is used for the conversion to molecular weight with reference to the book "SAIZU HAIJO KUROMATOGURAFI" (Size-eliminated Chromatography) written by Sadao Mori (KYORITSU SHUPPAN). In the equation for viscosity ($[\eta]=K\times M^\alpha$) to be used here, the following values are used.

(i) In drawing a calibration curve using standard polystyrene $K=0.000138$, $\alpha=0.70$
(ii) In measuring a sample of a propylene based block copolymer $K=0.000103$, $\alpha=0.78$ The distribution of ethylene content in each eluted component (the distribution of ethylene content along the axis of molecular weight) is determined using a ratio of absorbance at 2,956 cm$^{-1}$ and absorbance at 2927 cm$^{-1}$ obtained by GPC-IR and converting it to an ethylene polymerization ratio (% by mole) using a working curve prepared in advance. The working curve is prepared using polyethylene, polypropylene, an ethylene-propylene copolymer (EPR) in which the content of ethylene is known by $^{13}$C-NMR measurement and a mixture of these polymers.

(3-5) CP Content

The CP content in a block copolymer in the present invention is defined by equation (1) below and obtained by the following procedures.

$$CP\ content(\%\ by\ weight) = W40 \times A40/B40 + W100 \times A100/B100 \quad (1)$$

In equation (1), W40 and W100 are an elution ratio (unit: % by weight) in each above-described fraction; A40 and A100 are an observed average ethylene content (unit: % by weight) in each fraction corresponding to W40 and W100 respectively; and B40 and B100 are an ethylene content (unit: % by weight) in the CP contained in each fraction. It will be described later how to obtain A40, A100, B40 and B100.

The meaning of equation (1) is as follows. That is, the first term on the right side of equation (1) is a term for calculating an amount of the CP contained in fraction 1 (fraction soluble at 40° C.). If fraction 1 contains only a CP without containing a PP at all, W40 itself contributes to the content of the CP derived from fraction 1 in the whole block copolymer. In contrast, because a small amount of the components (components having extremely a low molecular weight and atactic polypropylene) derived from the PP are contained besides the components derived from the CP in fraction 1, W40 is necessary to be compensated said parts. Therefore, an amount of CP-derived components in fraction 1 is obtained by multiplying W40 by A40/B40. For example, when an average ethylene content (A40) in fraction 1 is 30% by weight and an ethylene content (B40) in the CP contained in fraction 1 is 40% by weight, it is concluded that $^{30}/_{40}=^3/_4$ (that is, 75% by weight) of fraction 1 is derived from the CP, whereas ¼ of fraction 1 is derived from the PP. Thus, an operation of multiplying A40/B40 in the first term on the right side means calculating a contribution of the CP from the percent by weight (W40) of fraction 1.

Things are similar for the second term on the right side. The contribution of the CP to each fraction is calculated and summed up to obtain the CP content.

The average ethylene contents in fractions 1 to 3, A40, A100 and A140 are respectively obtained by summing up the product of the weight ratio of each data point in a chromatogram of absorbance at 2,945 cm$^{-1}$ and the ethylene content (which can be obtained from the ratio of absorbance at 2,956 cm$^{-1}$ and 2,927 cm$^{-1}$) at each data point.

Let an ethylene content corresponding to the peak position in the differential molecular weight distribution curve of fraction 1 be B40 (unit is % by weight). As all rubber portions will be eluted at 40° C., in fraction 2, similar definition can not be applied. In the present invention, therefore, B100=100 is defined. It is practically impossible to obtain B40 and B100 by analysis which are an ethylene content in the CP contained in each fraction, because there is no means to perfectly separate a PP and a CP coexisting in the fraction.

After studying on various model samples, it has been found that if B40 is defined as an ethylene content corresponding to the peak position in the differential molecular weight distribution curve of fraction 1, the results of improvement of material properties turn out to be very reasonable. In addition, by the two reasons, in which B100 has a crystallizability derived from an ethylene chain and amount of CP contained in these fractions is smaller compared with the CP contained in fraction 1, approximation of B100 to be 100 is close to the actual state and causes few errors in calculation.

Analysis is thus conducted based on B100=100. The CP content, therefore, can be calculated according to equation (2) below.

$$CP\ content(\%\ by\ weight) = W40 \times A40/B40 + W100 \times A100/100 \quad (2)$$

That is, the first term (W40×A40/B40) on the right side shows the content (% by weight) of the CP having no crystallizability and the second term (W100×A100/100) shows the content (% by weight) of the CP having crystallizability.

The ethylene content in a copolymer component is obtained in equation (3) below using the content of the copolymer component obtained in equation (2).

$$\text{Ethylene content in the copolymer component}(\%\ \text{by weight}) = (W40 \times A40 + W100 \times A100 + W140 \times A140)/[\text{content of the copolymer component}(\%\ \text{by weight})] \quad (3)$$

Incidentally, the significance of setting above three kinds of fractionation temperature is as follows. In the CFC analysis relevant to the present invention, the temperature of 40° C. has significance of a necessary and sufficient temperature for fractionating only a polymer having no crystallizability (for example, most of CP, or a component having extremely low molecular weight and an atactic component among propylene polymer components (PP)). In addition, the temperature of 100° C. is a necessary and sufficient temperature for eluting only a component that is insoluble at 40° C., but soluble at 100° C. (for example, a component having crystallizability derived from ethylene and/or propylene chains in the CP, and the PP having low crystallizability). The temperature of 140° C. is a necessary and sufficient temperature for eluting only a component that is insoluble at 100° C., but soluble at 140° C. (for example, a component having especially high crystallizability in the PP and a component having an extremely high molecular weight and very high ethylene crystallizability in the CP) and recovering the whole amount of a block copolymer to be used in analysis. Incidentally, because the CP component is not present at all or is present in an extremely small amount to be practically negligible in W140, it is omitted from the calculation for a CP content and an ethylene content.

(3-6) Ethylene Polymerization Ratio

The ethylene content in the CP is obtained in the following equation.

Ethylene content in the $CP$ (% by weight)=$(W40 \times A40 + W100 \times A100)/[CP]$

[CP] is the CP content (% by weight) obtained previously.

(4) Measurement of Intrinsic Viscosity

The intrinsic viscosities of a crystalline propylene polymer portion ($[\eta]_{homo}$) and an ethylene-α-olefin copolymer portion ($[\eta]_{cp}$) in a propylene/ethylene-α-olefin block copolymer in the present invention are measured with an Ubbelohde viscosimeter at 135° C. using decalin as a solvent.

Firstly, the intrinsic viscosity $[\eta]_{homo}$ of a sample taken from a polymerization reactor is measured after polymerization of a crystalline propylene polymer portion. Secondly, the intrinsic viscosity $[\eta]F$ of a final polymer (F) obtained by polymerizing an ethylene-α-olefin copolymer after polymerization of the crystalline propylene polymer portion is measured. The $[\eta]_{cp}$ is obtained from the following relation.

$[\eta]F = (100-CP \text{ content})/100 \times [\eta]_{homo} + CP \text{ content}/100 \times [\eta]_{cp}$ Example 1

(1) Metallocene Complex: Synthesis of dichloro{1,1'-dimethylsilylene(2,3,5-trimethylcyclopentadienyl)(2-methyl-4-phenyl-4H-azulenyl)}hafnium 2-Methylazulene (1.42 g, 10.0 mmol) was dissolved in hexane (30 mL) and added dropwise at 0° C. with a solution (5.3 mL, 2.0 M) of phenyllithium in dibutyl ether. After dropwise addition, the resultant solution was warmed to room temperature and stirred for about one hour. The suspended reaction solution was left for standing and then a supernatant liquid was removed. The solution was added with hexane, stirred and left for standing and then a supernatant liquid was removed. After repeating this operation two times, the solution was added with tetrahydrofuran (30 mL), hexane (30 mL) and N-methylimidazole (0.02 mL) and added dropwise at −5° C. with chlorodimethyl(2,3,5-trimethylcyclopentadienyl)silane (1.95 g, 9.7 mmol). After dropwise addition, the resultant solution was warmed to room temperature, stirred for one hour and then added with distilled water and extracted with diethyl ether. After dried with magnesium sulfate, the organic layer had the solvent distilled off under reduced pressure to obtain a crude product (4.01 g) of dimethyl(2,3,5-trimethylcyclopentadienyl)(2-methyl-4-phenyl-1,4-dihydroazulenyl)silane.

The obtained ligand (4.01 g) was dissolved in diethyl ether (50 mL) and added dropwise at −10° C. with a solution (1.60 M, 12.1 mL) of n-butyllithium in n-hexane. After stirred at room temperature for 2 hours, the resultant solution was added with toluene (400 mL), cooled to −60° C., added with hafnium tetrachloride (3.10 g, 9.7 mmol), warmed slowly and stirred at room temperature for 2.5 hours. The obtained reaction solution was concentrated once, extracted with dichloromethane and concentrated again to dryness. The obtained substance was washed repeatedly with diethyl ether and subjected to recrystallization from toluene to obtain 0.46 g of the object dichloro{1,1'-dimethylsilylene(2,3,5-trimethylcyclopentadienyl)(2-methyl-4-phenyl-4H-azulenyl)}hafnium (anti:syn=85:15).

$^1$HNMR (400 MHz, CDCl$_3$): δ0.95 (s, 3H, Si(CH$_3$)$_2$), 1.00 (s, 3H, Si(CH$_3$)$_2$), 2.07 (s, 3H, Cp-2-CH$_3$), 2.14 (s, 3H, Azu-2-CH$_3$), 2.18 (s, 3H, Cp-3-CH$_3$), 2.34 (s, 3H, Cp-5-CH$_3$), 5.04 (d, J=3.0 Hz, 1H, Azu -4-H), 5.77 (s, 1H, Azu-3-H), 5.85-5.95 (m, 2H, Azu-5H, 6H), 6.10 (dd, 1H, Azu-7H), 6.46 (s, 1H, Cp-4-H), 6.85 (d, 1H, Azu-8-H), 7.26 (t, 1H, Ph-p -H), 7.35 (t, 2H, Ph-m-H), 7.45 (t, 2H, Ph-o-H).

(2) Catalyst Preparation

In a 5 L separable flask equipped with a stirrer and a reflux apparatus, 1,698 g of pure water was filled and 501 g of 98% sulfuric acid was added dropwise. The resultant solution was further added with 300 g of commercially available granular montmorillonite (made by MIZUSAWA INDUSTRIAL CHEMICALS, LTD., BENCLAY SL, average particle diameter: 19.5 μm), stirred and then subjected to reaction at 90° C. for 2 hours. The obtained slurry was washed in an apparatus equipped with an aspirator connected to Nutsche and a suction bottle. The recovered cake was added with an aqueous solution of 324 g of lithium sulfate monohydrate in 900 mL of water and subjected to reaction at 90° C. for 2 hours. The resultant slurry was washed in an apparatus equipped with an aspirator connected to Nutsche and a suction bottle until the pH becomes higher than 4. The recovered cake was dried overnight at 120° C. to obtain 275 g of a chemically-treated material.

10.0 g of the above obtained chemically-treated montmorillonite was weighed in a flask of 1 L of an internal volume and added with 65 mL of heptane and 35.4 mL (25 mmol) of a solution of triisobutylaluminum in heptane and stirred at room temperature for one hour. The liquid was then washed off with heptane till 1/100 in amount to prepare 100 mL of slurry finally.

(3) Prepolymerization by Propylene

The above prepared heptane slurry of montmorillonite treated with triisobutylaluminum was added with 0.85 mL of a solution of triisobutylaluminum in heptane and stirred at room temperature for 10 minutes. A solution of the dichloro{1,1'-dimethylsilylene(2,3,5-trimethylcyclopentadienyl)(2-methyl-4-phenyl-4H-azulenyl)}hafnium (300 μmol) synthesized in (1) in toluene (60 mL) was added into the above 1 L flask and stirred at room temperature for 60 minutes.

The above heptane slurry of montmorillonite was then further added with 340 mL of heptane and introduced to an autoclave equipped with a stirrer of 1 L of an internal volume, to which propylene was supplied at 40° C. at a constant rate of 238.1 mmol/hr (10 g/hr) for 120 minutes. After propylene supply, the autoclave was heated to 50° C. and left as it was for 2 hours. Subsequently, a remaining gas was purged off and the prepolymerized catalyst slurry was recovered from the autoclave. The recovered prepolymerized catalyst slurry was left for standing and a supernatant liquid was removed. A solid left behind was added with 8.5 mL (6.0 mmol) of a solution of triisobutylaluminum in heptane at room temperature, stirred at room temperature for 10 minutes and then dried under reduced pressure to recover 31.98 g of a solid catalyst.

The ratio of the polymer to the solid catalyst (the value obtained by dividing the amount of the prepolymerized polymer by the amount of the solid catalyst) was 2.14.

(4) Block Polymerization by Ethylene-Propylene Copolymerization

After fully displacing the air in an autoclave equipped with a stirrer of 3 L of an internal volume with propylene, 2.76 mL (2.02 mmol) of a solution of triisobutylaluminum in n-heptane was added, then added with 90 mL of hydrogen and subsequently 750 g of liquid propylene and heated to 65° C. and kept at this temperature. The prepolymerized catalyst prepared in the above (3) was slurried with normal heptane and 50 mg (excluding the weight of a prepolymerized polymer) was pressed into the autoclave as a catalyst to initiate polymerization. After one hour since catalyst charge while keeping the internal temperature at 65° C., remaining monomers were purged off and the gas in the autoclave was displaced 5 times with argon. Stirring was stopped and a Teflon® tube was inserted into the autoclave to withdraw a small amount of polypropylene under argon flow. Weighing after drying under nitrogen flow at 90° C. for 30 minutes showed that the amount of withdrawn polypropylene was 18 g.

Subsequently, propylene was introduced until 0.7 MPa, and then ethylene was introduced until 1.3 MPa. After raising internal temperature to 80° C., a mixed gas of propylene and ethylene prepared in advance was introduced. The polymerization reaction was controlled for 30 minutes, keeping the composition ratio of the monomers constant at an internal pressure of 2.0 MPa during polymerization to obtain 85 g of a propylene/ethylene-propylene based block copolymer having good particle properties.

According to the results of CFC-IR, the above obtained propylene/ethylene-propylene based block copolymer had a rubber content (CP content) of 6.6% by weight, an ethylene content in rubber (CP) of 52.0% by mole, an MFR of 3.4 (dg/minute) and a weight average molecular weight of the CP portion of 320,000. The propylene homopolymer separately sampled had a Tm of 155.6° C. and an MFR of 3.93.

Example 2

(1) Metallocene Complex: Synthesis of dichloro{1,1'-dimethylsilylene(2-methyl-4-phenylcyclopentadienyl)(2-methyl-4-phenyl-4H-azulenyl)}hafnium 2-Methylazulene (1.42 g, 10.0 mmol) was dissolved in hexane (30 mL) and added dropwise at 0° C. with a solution (9.5 mL, 1.0 M) of phenyllithium in cyclohexane-diethyl ether. After dropwise addition, the resultant solution was warmed to room temperature and stirred for about one hour. The suspended reaction solution was left for standing and then a supernatant liquid was removed. The solution was added with hexane and left for standing and then a supernatant liquid was removed. After repeating this operation two times, the solution was added with tetrahydrofuran (30 mL), hexane (30 mL) and N-methylimidazole (0.02 mL) and added dropwise at −5° C. with chlorodimethyl(2-methyl-4-phenyl-cyclopentadienyl)silane (2.49 g, 10 mmol). After dropwise addition, the resultant solution was warmed to room temperature, stirred for one hour and then added with distilled water and extracted with diethyl ether. After dried with magnesium sulfate, the organic layer had the solvent distilled off under reduced pressure to obtain a crude product (4.28 g) of dimethyl(2-methyl-4-phenylcyclopentadienyl)(2-methyl-4-phenyl-1,4-dihydroazulenyl)silane.

The obtained ligand (4.28 g) was dissolved in diethyl ether (50 mL) and added dropwise at −10° C. with a solution (1.60 M, 12.4 mL) of n-butyllithium in n-hexane. After stirred at room temperature for 2 hours, the resultant solution was added with toluene (400 mL), cooled to −60° C., added with hafnium tetrachloride (3.17 g, 9.9 mmol), warmed slowly and stirred at room temperature for 2 hours. The obtained reaction solution was concentrated once, extracted with toluene and concentrated again to dryness. The obtained substance was extracted several times with diisopropyl ether and further extracted several times with a mixed solvent of toluene and hexane, and then washed several times with n-hexane and further washed several times with diisopropyl ether to obtain 0.23 g of the object dichloro{1,1'-dimethylsilylene(2-methyl-4-phenylcyclopentadienyl)(2-methyl-4-phenyl-4H-azulenyl)}hafnium (anti pure).

$^1$HNMR (400 MHz, CDCl$_3$): δ0.87 (s, 3H, Si(CH$_3$)$_2$), 1.01 (s, 3H, Si(CH$_3$)$_2$), 2.15 (s, 3H, Azu-2-CH$_3$), 2.41 (s, 3H, Cp-2-CH$_3$), 5.07 (d, J=3.0 Hz, 1H, Azu-4-H), 5.64 (s, 1H, Azu-3-H), 5.73 (s, 1H, Cp-3-H), 5.95 (m, 2H, Azu-5H, 6H), 5.97 (dd, 1H, Azu-7-H), 6.77 (d, 1H, Azu-8-H), 6.86 (s, 1H, Cp-5-H), 7.20-7.36 (m, 10H, arom)

(2) Prepolymerization and Block Polymerization by Ethylene-Propylene Copolymerization A prepolymerized catalyst was prepared similarly to (2) and (3) of Example 1 except that the above synthesized dichloro{1,1'-dimethylsilylene(2-methyl-4-phenylcyclopentadienyl)(2-methyl-4-phenyl-4H-azulenyl)}hafnium was used. The ratio of the polymer to the solid catalyst (value obtained by dividing the amount of the prepolymerized polymer by the amount of the solid catalyst) was 2.18.

Subsequently, polymerization was carried out similarly to (4) of Example 1 to obtain 10.1 g of a polymer withdrawn at the end of the first-stage polymerization and 86 g of a propylene/ethylene-propylene based block copolymer. According to the results of CFC-IR, the obtained propylene/ethylene-propylene based block copolymer had a rubber content (CP content) of 5.2% by weight, an ethylene content in rubber (CP) of 58.0% by mole, an MFR of 55.4 (dg/minute) and a weight average molecular weight of the CP portion of 380,000. The propylene homopolymer separately sampled had a Tm of 150.8° C. and an MFR of 77.9.

Example 3

(1) Metallocene Complex: Synthesis of dichloro{1,1'-dimethylsilylene(2-methyl-4-(3,5-dimethylphenyl)cyclopentadienyl)(2-methyl-4-phenyl-4H-azulenyl)}hafnium 1-Bromo-3,5-dimethylbenzene (13.6 g, 73.6 mmol) was dissolved in a mixed solution of hexane (150 mL) and diethyl ether (20 mL) and added dropwise at 0° C. with a solution (46.6 mL, 1.58M) of n-butyllithium in hexane. The solution was immediately warmed to room temperature, stirred night and day and added dropwise at −78° C. to a solution of 3-methyl-2-cyclopentanone (7.3 mL, 74 mmol) in diethyl ether (100 mL). The resultant solution was warmed to room temperature immediately after dropwise addition and stirred for 2 hours. After termination of the reaction, the reaction solution was added with dilute hydrochloric acid, stirred at room temperature for 30 minutes and then subjected to layer separation. The organic layer was dried with magnesium sulfate and then had the solvent distilled off under reduced pressure. The crude product was distilled under reduced pressure (125 to 127° C./0.5 mmHg) to obtain 1-methyl-3-(3,5-dimethyl-phenyl)-cyclopentadiene (6.2 g, yield: 46%).

The above obtained 1-methyl-3-(3,5-dimethyl-phenyl)-cyclopentadiene (6.2 g, 33 mmol) was dissolved in diethyl ether (100 mL), ice-cooled and added dropwise with a solution (21.2 mL, 1.50 M) of n-butyllityium in hexane, warmed to room temperature and then stirred for 4 hours. The reaction solution was added dropwise at −72° C. to a solution of dimethylsilyl dichloride (15 mL) in tetrahydrofuran (200 mL) and stirred at room temperature night and day. After termination of the reaction, the reaction solution was extracted with diethyl ether and distilled under reduced pressure (145° C./0.5 mmHg) to obtain 1-(chlorodimethylsilyl)-2-methyl-4-(3,5-dimethyl-phenyl)-cyclopentadiene (5 g, yield: 54%).

2-Methylazulene (2.6 g, 18 mmol) was dissolved in hexane (80 mL), added dropwise with a solution (15.8 mL, 1.44 M) of phenyllithium in cyclohexane-diethyl ether while cooled on ice and immediately warmed to room temperature and stirred for 2 hours. Subsequently, the obtained solution was added with tetrahydrofuran (90 mL) and N-methylimidazole (0.02 mL), cooled again to 0° C. and added dropwise with a solution of the above obtained 1-(chlorodimethylsilyl)-2-methyl-4-(3, 5-dimethyl-phenyl)-cyclopentadiene in tetrahydrofuran (5 mL). The resultant solution was stirred at room temperature for 1.5 hours and then quenched with water, subjected to layer separation, dried with magnesium sulfate and had the solvent distilled off under reduced pressure.

The obtained crude product (8 g) was dissolved in diisopropyl ether (40 mL) and added dropwise at −2° C. with a solution (22.5 mL, 1.58 M) of n-butyllithium in hexane. The obtained solution was stirred at room temperature for one hour and then added with toluene (240 mL), cooled to −78° C., added with hafnium tetrachloride (5.7 g, 17.8 mmol), warmed and stirred at room temperature for 4 hours. The obtained reaction solution was concentrated once, extracted with toluene and concentrated again to dryness. The resultant substance was washed diethyl ether and then extracted again with toluene, concentrated to dryness to obtain dichloro{1, 1'-dimethylsilylene(2-methyl-4-(3,5-dimethylphenyl)cyclopentadienyl)(2-methyl-4-phenyl-4H-azulenyl)}hafnium (anti/syn=1/0.1, 0.6 g, yield: 4%).

$^1$HNMR (400 MHz, CDCl$_3$) δ 0.88 (s, 3H, SiCH$_3$), 1.00 (s, 3H, SiCH$_3$), 2.17 (3, 3H, 2-Me), 2.29 (s, 6H, 3,5-Me$_2$Ph), 2.40 (s, 3H, 2-Me), 5.08 (s, 1H, azulene-4-H), 5.6-6.3 (m, 4H), 6.6-7.1 (m, 3H), 7.1-7.5 (m, 8H, arom-H).

(2) Prepolymerization and Block Polymerization by Ethylene-Propylene Copolymerization A prepolymerized catalyst was prepared similarly to (2) and (3) of Example 1 except that the above synthesized dichloro{1,1'-dimethylsilylene(2-methyl-4-(3,5-dimethylphenyl)cyclopentadienyl)(2-methyl-4-phenyl-4H-azulenyl)}hafnium was used. The ratio of the polymer to the solid catalyst (value obtained by dividing the amount of the prepolymerized polymer by the amount of the solid catalyst) was 2.04.

Subsequently, polymerization was carried out similarly to (4) of Example 1 to obtain 10.4 g of a polymer withdrawn at the end of the first-stage polymerization and 141 g of a propylene/ethylene-propylene based block copolymer. According to the results of CFC-IR, the obtained propylene/ethylene-propylene based block copolymer had a rubber content (CP content) of 13.8% by weight, an ethylene content in rubber (CP) of 53.5% by mole, an MFR of 5.7 (dg/minute) and a weight average molecular weight of the CP portion of 330,000. The propylene homopolymer separately sampled had a Tm of 152.7° C. and an MFR of 9.8.

Example 4

(1) Metallocene Complex: synthesis of dichloro{1,1'-dimethylsilylene(2-methyl-4-(4-t -butylphenyl)cyclopentadienyl)(2-methyl-4-phenyl-4H-azulenyl)}hafnium 1-Bromo-4-t-butylbenzene (18 mL, 104 mmol) was dissolved in diethyl ether (100 mL) and added dropwise at −30° C. with a solution (66 mL, 104 mmol, 1.57 N) of n-butyllithium in hexane. The resultant solution was warmed to room temperature, stirred night and day and added dropwise at −20° C. to a solution of 3-methyl-2-cyclopentanone (10 g, 104 mmol) in diethyl ether (10 mL). Immediately after dropwise addition, the solution was warmed to room temperature and stirred for 3 hours. After termination of the reaction, the reaction solution was added with dilute hydrochloric acid and subjected to layer separation. The organic layer was dried with magnesium sulfate and then had the solvent distilled off under reduced pressure. The crude product was distilled under reduced pressure (105 to 115° C./0.16 mmHg) to obtain 1-methyl-3-(4-t-butylphenyl)-cyclopentadiene (15.3 g, yield: 69%).

The above obtained 1-methyl-3-(4-t-butylphenyl)-cyclopentadiene (30.4 g, 14.3 mmol) was dissolved in a mixed solvent of hexane (25 mL) and diethyl ether (5 mL), ice-cooled, added dropwise with a solution (9.1 mL, 14.3 mmol, 1.57 N) of n-butyllithium in hexane, warmed to room temperature and then stirred for 1.5 hours. The reaction solution was added dropwise at −60° C. with a solution of dimethylsilyl dichloride (1.9 mL, 15.7 mmol) in tetrahydrofuran (20 mL) and stirred at room temperature night and day. After termination of the reaction, the obtained solution was extracted with diethyl ether and had the solvent distilled off to obtain a crude product (4.28 g) of 1-(chlorodimethylsilyl)-2-methyl-4-(4-t-butylphenyl)cyclopentadiene.

2-Methylazulene (1.59 g, 11.2 mmol) was dissolved in hexane (40 mL), added dropwise with a solution (11.3 mL, 11.9 mmol) of phenyllithium in cyclohexane-diethyl ether while cooled on ice and immediately warmed to room temperature and stirred for one hour. Subsequently, the obtained solution was added with tetrahydrofuran (10 mL) and N-methylimidazole (0.02 mL), cooled again to 0° C. and added dropwise with a solution of the above obtained crude product of 1-(chlorodimethylsilyl)-2-methyl-4-(4-t-butylphenyl)cyclopentadiene in tetrahydrofuran (5 mL). The resultant solution was stirred at room temperature for 2 hours and then quenched with water, subjected to layer separation, dried with magnesium sulfate and had the solvent distilled off under reduced pressure. The resultant solution was purified with silica-gel column chromatography (solvent: hexane-dichloromethane 5:1) to obtain dimethyl(2-methyl-4-(4-t-butylphenyl)cyclopentadienyl)(2-methyl-4-phenyl-1,4-dihydroazulenyl)silane (3.82 g, yield: 70%).

The obtained product (3.82 g) was dissolved in diethyl ether (25 mL) and added dropwise at 0° C. with a solution (10 mL, 15.8 mmol, 1.57 N) of n-butyllithium in hexane. The resultant solution was stirred at room temperature for 2 hours and then added with toluene (125 mL), cooled to −10° C., added with hafnium tetrachloride (2.4 g, 7.5 mmol), then warmed and stirred at room temperature for 2 hours. The obtained reaction solution was concentrated once, extracted with diisopropyl ether (40 mL) and had the solvent distilled off. The resultant substance was washed with hexane (50 mL) and further with a mixed solvent of hexane (30 mL) and cyclohexane (30 mL) and concentrated again to dryness to obtain dichloro{1,1'-dimethylsilylene(2-methyl-4-(4-t -butylphenyl)cyclopentadienyl)(2-methyl-4-phenyl-4H-azulenyl)}hafnium (anti, 0.86 g, yield: 15%).

$^1$HNMR (400 MHz, CDCl$_3$) δ0.84 (s, 3H, Si (CH$_3$)$_2$), 1.01 (s, 3H, Si (CH$_3$)$_2$), 1.29 (s, 9H, t-Bu), 2.15 (s, 3H, CH$_3$), 2.40 (s, 3H, CH$_3$), 5.07 (br, 1H, Azu-4-H), 5.62 (s, 1H), 5.70 (s, 1H), 5.95-6.25 (m, 3H), 6.77 (d, 1H), 6.83 (s, 1H), 7.20-7.43 (m, 9H, arom).

(2) Prepolymerization and Block Polymerization by Ethylene-Propylene Copolymerization A prepolymerized catalyst was prepared similarly to (2) and (3) of Example 1 except that the above synthesized dichloro{1,1'-dimethylsilylene(2-methyl-4-(4-t -butylphenyl)cyclopentadienyl)(2-methyl-4-phenyl-4H-azulenyl)} hafnium was used. The ratio of the polymer to the solid catalyst (the value obtained by dividing the amount of the prepolymerized polymer by the amount of the solid catalyst) was 2.20.

Subsequently, polymerization was carried out similarly to (4) of Example 1 to obtain 6.3 g of a polymer withdrawn at the end of the first-stage polymerization and 84 g of a propylene/ethylene-propylene based block copolymer. According to the results of CFC-IR, the obtained propylene/ethylene-propylene based block copolymer had a rubber content (CP content) of 7.5% by weight, an ethylene content in rubber (CP) of 54.5% by mole, an MFR of 31 (dg/minute) and a weight average molecular weight of the CP portion of 350,000. The propylene homopolymer separately sampled had a Tm of 150.9° C. and an MFR of 42.

Example 5

(1) Metallocene Complex: Synthesis of dichloro{1,1'-dimethylsilylene(2-methyl-4-phenylcyclopentadienyl)(2-ethyl-4-phenyl-4H-azulenyl)}hafnium 2-Ethylazulene (3.12 g, 20.0 mmol) was dissolved in hexane (65 mL) and added dropwise at 0° C. with a solution (18.4 mL, 1.14M) of phenyllithium in cyclohexane-diethyl ether. After dropwise addition, the resultant solution was warmed to room temperature, stirred for about 3 hours and then added with tetrahydrofuran (45 mL) and N-methylimidazole (0.08 mL) and added dropwise at 0° C. with chlorodimethyl(2-methyl-4-phenyl-2,4-cyclopentadienyl)silane (5.01 g, 20.1 mmol). After dropwise addition, the obtained solution was warmed to room temperature, stirred for 2 hours and then added with distilled water and had the water layer withdrawn. The organic layer was dried with magnesium sulfate and had the solvent distilled off under reduced pressure to obtain a crude product (8.24 g) of dimethyl(2-methyl-4-phenylcyclopentadienyl)(2-ethyl-4-phenyl-1,4-dihydroazulenyl)silane.

The obtained crude product (8.24 g) was dissolved in diethyl ether (40 mL) and added dropwise at 0° C. with a solution (1.58 M, 23.3 mL) of n-butyllithium in hexane. The resultant solution was stirred at room temperature for 2 hours and then added with toluene (320 mL), cooled to −78° C., added with hafnium tetrachloride (5.86 g, 18.3 mmol), then warmed slowly and stirred at room temperature for 2 hours. The obtained reaction solution was concentrated once, extracted with toluene and concentrated again to dryness. The resultant substance was washed with toluene and then with cyclohexane to obtain the object dichloro{1,1'-dimethylsilylene(2-methyl-4-phenylcyclopentadienyl)(2-ethyl-4-phenyl-4H-azulenyl)}hafnium (syn:anti=9:91, 1.36 g, yield: 10%).

$^1$HNMR (400 MHz, CDCl$_3$) δ 0.84 (s, 3H, Si (CH$_3$)$_2$), 1.01 (s, 3H, Si (CH$_3$)$_2$), 1.04 (dd, 3H, Azu-2-CH$_2$CH$_3$), 2.35 (dq, 1H, Azu-2-CH$_2$CH$_3$), 2.40 (s, 3H, C p-2-CH$_3$), 2.60 (dq, 1H, Azu-2-CH$_2$CH$_3$), 5.09 (d, J=1.8 Hz, 1H, Azu-4-H), 5.67 (s, 1H, Azu-3-H), 5.75 (s, 1H, Cp-3-H), 5.94-5.98 (m, 2H, Azu-5H, 6H), 6.22 (dd, 1H, Azu-7-H), 6.77 (d, 1H, Azu-8-H), 6.84 (s, 1H, Cp-5-H), 7.20-7.43 (m, 10H, arom).

(2) Prepolymerization and Block Polymerization by Ethylene-Propylene Copolymerization A prepolymerized catalyst was prepared similarly to (2) and (3) of Example 1 except that the above synthesized dichloro{1,1'-dimethylsilylene(2-methyl-4-phenylcyclopentadienyl)(2-ethyl-4-phenyl-4H-azulenyl)}hafnium was used. The ratio of the polymer to the solid catalyst (the value obtained by dividing the amount of the prepolymerized polymer by the amount of the solid catalyst) was 2.05.

Subsequently, polymerization was carried out similarly to (4) of Example 1 to obtain 9.6 g of a polymer withdrawn at the end of the first-stage polymerization and 121 g of a propylene/ethylene-propylene based block copolymer. According to the results of CFC-IR, the obtained propylene/ethylene-propylene based block copolymer had a rubber content (CP content) of 8.9% by weight, an ethylene content in rubber (CP) of 55.2% by mole, an MFR of 22 (dg/minute) and a weight average molecular weight of the CP portion of 340,000. The propylene homopolymer separately sampled had a Tm of 150.78° C. and an MFR of 35.

Example 6

(1) Metallocene Complex: Synthesis of dichloro{1,1'-dimethylsilylene(3-t-butyl-5-methylcyclopentadienyl)(2-methyl-4-phenyl-4H-azulenyl)}hafnium 2-Methylazulene (6.63 g, 46.7 mmol) was dissolved in hexane (100 mL) and added dropwise at 0° C. with a solution (41 mL, 46.7 mmol, 1.14M) of phenyllithium in cyclohexane-diethyl ether. After dropwise addition, the resultant solution was warmed to room temperature, stirred for about one hour. The suspended reaction solution was left for standing and then a supernatant liquid was removed. The solution was added with hexane and left for standing and then a supernatant liquid was removed. After repeating this operation two times, the solution was added with tetrahydrofuran (50 mL), hexane (100 mL) and N-methylimidazole (0.1 mL) and added dropwise at 5° C. with chlorodimethyl(3-tert-butyl-5-methyl-2,4-cyclopentadienyl)silane (10.0 g, 46.7 mmol). After dropwise addition, the obtained solution was warmed to room temperature, stirred for one hour and then added with distilled water and extracted with diethyl ether. The organic layer was dried with magnesium sulfate and had the solvent distilled off under reduced pressure to obtain a crude product (19.6 g) of dimethyl(3-tert-butyl-5-methylcyclopentadienyl)(2-methyl-4-phenyl-1,4-dihydroazulenyl)silane.

The obtained product (19.6 g) was dissolved in diethyl ether (50 mL) and added dropwise at −5° C. with a solution (93.4 mmol, 1.59 M, 58.7 mL) of n-butyllithium in hexane. The resultant solution was stirred at room temperature for 2 hours and then added with toluene (400 mL), cooled to −60° C., added with hafnium tetrachloride (14.9 g, 46.7 mmol), then warmed slowly and stirred at room temperature for 4 hours. The obtained reaction solution was concentrated once, washed with diisopropyl ether, ethanol and then diisopropyl ether to obtain dichloro{1,1'-dimethylsilylene(3-tert-butyl-5-methylcyclopentadienyl)(2-methyl-4-phenyl-4H-azulenyl)} hafnium (anti/syn=46/54, 15.94 g).

This anti/syn mixture (8.67 g) was extracted with toluene and the extract was recrystallized from methylene chloride. The recrystallized substance was washed with toluene to obtain the object dichloro{1,1'-dimethylsilylene(3-tert-butyl-5-methylcyclopentadienyl)(2-methyl-4-phenyl-4H-azulenyl)}hafnium (anti pure, 0.07 g, yield: 0.2%).

$^1$HNMR (400 MHz, CDCl$_3$) δ 0.84 (s, 6H, Si (CH$_3$)$_2$), 0.94 (s, 6H, Si (CH$_3$)$_2$), 1.25 (s, 9H, Cp-3-t-Bu), 2.17 (s, 3H, Azu-2-CH$_3$), 2.33 (s, 3H, Cp-5-CH$_3$), 5.07 (d, 1H, Azu-4H), 5.47 (d, 1H, Cp-4-H), 5.61 (s, Azu-3-H), 5.88-5.98 (m, 2H), 6.14-6.19 (dd, 2H), 6.48 (d, 1H, Cp-2-H), 6.71 (d, 1H, Azu-8-H), 6.86 (dd, 1H), 7.28 (t, 1H, p-Ph-H), 7.36 (t, 2H, m-Ph-H), 7.45 (d, 2H, o-Ph-H)

(2) Prepolymerization and Block Polymerization by Ethylene-Propylene Copolymerization A prepolymerized catalyst was prepared similarly to (2) and (3) of Example 1 except that the above synthesized dichloro{1,1'-dimethylsilylene(3-t-butyl-5-methylcyclopentadienyl)(2-methyl-4-phenyl-4H-azulenyl)}hafnium was used. The ratio of the polymer to the solid catalyst (the value obtained by dividing the amount of the prepolymerized polymer by the amount of the solid catalyst) was 0.4.

Subsequently, polymerization was carried out similarly to (4) of Example 1 to obtain 3 g of a propylene/ethylene-propylene based block copolymer without withdrawing a polymer at the end of the first-stage polymerization. According to the results of CFC-IR, the obtained propylene/ethylene-propylene based block copolymer had a rubber content (CP content) of 26% by weight, an ethylene content in rubber (CP) of 70% by mole and a weight average molecular weight of the CP portion of 380,000.

Example 7

(1) Metallocene Complex: Synthesis of dichloro{1,1'-dimethylsilylene(2-methyl-4-isopropylcyclopentadienyl)(2-methyl-4-phenyl-4H-azulenyl)}hafnium 2-Methylazulene (7.86 g, 55.3 mmol) was dissolved in hexane (180 mL) and added dropwise at 0° C. with a solution (53.4 mL, 1.14M) of phenyllithium in cyclohexane-diethyl ether. After dropwise addition, the resultant solution was warmed to room temperature, stirred for about 2 hours. The suspended reaction solution was left for standing and then a supernatant liquid was removed. The solution was added with hexane, stirred and left for standing and then a supernatant liquid was removed. After repeating this operation two times, the solution was added with tetrahydrofuran (50 mL), hexane (110 mL) and N-methylimidazole (0.22 mL) and added dropwise at 0° C. with chlorodimethyl(2-methyl-4-isopropylcyclopentadienyl)silane (11.9 g, 55.3 mmol). After dropwise addition, the obtained solution was warmed to room temperature, stirred for 2.5 hours and then added with distilled water followed by removal of the water layer. The organic layer was dried with magnesium sulfate and had the solvent distilled off under reduced pressure to obtain a crude product (21.86 g) of dimethyl(2-methyl-4-isopropylcyclopentadienyl)(2-methyl-4-phenyl-1,4-dihydroazulenyl)silane.

The obtained crude product (21.86 g) was dissolved in diethyl ether (80 mL) and added dropwise at 0° C. with a solution (1.58 M, 69.4 mL) of n-butyllithium in hexane. The resultant solution was stirred at room temperature for 2 hours and then added with toluene (640 mL), cooled to −78° C., added with hafnium tetrachloride (17.6 g, 54.8 mmol), then warmed slowly and stirred at room temperature for 2 hours. The obtained reaction solution was concentrated once, extracted with toluene, and concentrated again to dryness. The obtained substance was washed with hexane and then with diisopropyl ether, and further several times with a mixed solvent of toluene and hexane followed by washing with cyclohexane to obtain the object dichloro{1,1'-dimethylsilylene(2-methyl-4-isopropylcyclopentadienyl)(2-methyl-4-phenyl-4H-azulenyl)}hafnium (anti:syn=18:82, 6.75 g, yield: 19%).

$^1$HNMR (400 MHz, CDCl$_3$) δ0.81 (s, 3H, Si(CH$_3$)$_2$) 0.96 (s, 3H, Si(CH$_3$)$_2$), 1.09 (d, 3H, Cp-4-CH(CH$_3$)$_2$), 1.20 (d, 3H, Cp-4-CH(CH$_3$)$_2$), 2.10 (s, 3H, Azu-2-CH$_3$), 2.33 (s, 3H, Cp-2-CH$_3$), 3.03 (tt, 1H, Cp-4-CH(CH$_3$)$_2$), 5.07 (d, J=2.8 Hz, 1H, Azu-4-H), 5.26 (s, 1H, Azu-3-H), 5.65 (s, 1H, Cp-3-H), 5.82-5.97 (m, 2H, Azu-5H, 6H), 6.18 (dd, 1H, Azu-7-H), 6.40 (s, 1H, Cp-5-H), 6.74 (d, 1H, Azu-8-H), 7.30 (dd, 2H, Ph-m-H), 7.35 (t, 1H, Ph-p-H), 7.44 (d, 2H, Ph-o-H).

(2) Prepolymerization and Block Polymerization by Ethylene-Propylene Copolymerization A prepolymerized catalyst was prepared similarly to (2) and (3) of Example 1 except that the above synthesized dichloro{1,1'-dimethylsilylene(2-methyl-4-i-propylcyclopentadienyl)(2-methyl-4-phenyl-4H-azulenyl)}hafnium was used. The ratio of the polymer to the solid catalyst (the value obtained by dividing the amount of the prepolymerized polymer by the amount of the solid catalyst) was 1.89.

Subsequently, polymerization was carried out similarly to (4) of Example 1 to obtain 2.5 g of a polymer withdrawn at the end of the first-stage polymerization and 47 g of a propylene/ethylene-propylene based block copolymer. According to the results of CFC-IR, the obtained propylene/ethylene-propylene based block copolymer had a rubber content (CP content) of 8.6% by weight, an ethylene content in rubber (CP) of 56.5% by mole, an MFR of 50.6 (dg/minute) and a weight average molecular weight of the CP portion of 330,000. The propylene homopolymer separately sampled had a Tm of 153.6° C.

Example 8

(1) Catalyst Preparation

The dichloro{1,1'-dimethylsilylene(2-methyl-4-phenylcyclopentadienyl)(2-methyl-4-phenyl-4H-azulenyl)}hafnium (10 μmol) synthesized in (1) of Example 2 was dissolved in a solution (5 mL, 0.01 mol/L) of triisobutylaluminum in toluene and added with toluene (5 mL).

The amount of 200 mg of the chemically treated montmorillonite obtained in (2) of Example 1 was added with a solution (0.8 mL, 0.5 mol/L) of triethylaluminum in toluene and stirred at room temperature for 30 minutes. The resultant solution was then added with toluene (5 mL), stirred and then left for standing and a supernatant liquid was removed. The residual solution was added with toluene (5 mL) again, stirred and then left for standing and a supernatant liquid was removed.

The triethylaluminum-treated montmorillonite was added with the above complex solution (6 mL) and stirred at room temperature for one hour.

(2) Ethylene-Propylene Copolymerization

Purified hexane (700 mL) and a solution (1 mL, 0.5 mol/L) of triisobutylaluminum in toluene were introduced into an autoclave of 2 L of an internal volume that is equipped with an induction-stirrer and displaced with purified nitrogen. On the other hand, the slurry (3 mL) prepared in above (1) was introduced into a catalyst feeder equipped with a rupture disc. Another autoclave of 2 L of an internal volume was filled with a mixture (1/1) of ethylene and propylene to prepare a mixed gas vessel (internal pressure: 3.0 MPa) kept at 80° C. The polymerization tank was filled with the mixed gas up to 0.5 MPa, heated to 70° C., filled with the catalyst from the catalyst feeder by pressing with purified nitrogen and then filled with the mixed gas up to 0.8 MPa to initiate polymerization. The mixed gas was introduced successively to keep the polymerization tank at a pressure of 0.8 MPa and a polymerization temperature of 75° C. After continuing polymerization for 15 minutes, ethanol (20 mL) was introduced to terminate polymerization. The resultant polymer slurry had the solvent distilled off and was dried under reduced pressure at 80° C. for 2 hours to obtain 35 g of a polymer. The obtained ethylene-propylene copolymer had an ethylene content of 55.6% by mole and a weight average molecular weight of 285,000.

Example 9

(1) Block Polymerization by Ethylene-1-Butene Copolymerization

A solution (2.76 mL, 2.02 mmol) of triisobutylaluminum in n-heptane was introduced into an autoclave of 3 L of an internal volume equipped with a stirrer that was fully displaced with propylene, and added with 90 mL of hydrogen and then with 750 g of liquid propylene, heated to 70° C. and kept at the temperature. The prepolymerized catalyst prepared in (3) of Example 2 was slurried with normal heptane and 50 mg (excluding the weight of a prepolymerized polymer) of the slurry was pressed into the autoclave as a catalyst to initiate polymerization. After one hour since catalyst charge at an internal temperature of 70° C., remaining monomers were purged off and the gas in the autoclave was displaced 5 times with argon. Stirring was stopped and a Teflon® tube was inserted into the autoclave to withdraw a small amount of polypropylene under argon flow. Weighing after drying under nitrogen flow at 90° C. for 30 minutes showed that the amount of withdrawn polypropylene was 10 g.

On the other hand, an autoclave of 14 L of an internal volume equipped with a stirrer was kept at an internal temperature of 90° C. and filled with 1-butene (150 mL). Ethylene was pressed into the autoclave up to 3.5 MPa to prepare a mixed gas of 1-butene and ethylene.

After raising internal temperature of the above 3 L-autoclave used for propylene polymerization to 80° C., a mixed gas of 1-butene and ethylene prepared in advance was introduced. The polymerization reaction was controlled for 30 minutes, while supplying the mixed gas to keep the internal pressure at 2.0 MPa during polymerization.

As a result, 110 g of a propylene/ethylene-butene block copolymer having good particle properties was obtained.

According to the results of CFC-IR, the above obtained block copolymer had a rubber content (CP content) of 9.5% by weight, an MFR of 11.6 (dg/minute), an ethylene content in rubber (CP) of 89% by weight, a weight average molecular weight of the CP portion of 790,000 and an $[\eta]_{cp}$ of 5.10. The propylene homopolymer separately sampled had a Tm of 150.2° C. and an MFR of 18.3 (dg/minute).

Example 10

(1) Block Polymerization by Ethylene-1-Butene Copolymerization

Similar operation to above Example 9 was conducted except that the same prepolymerized catalyst as used in above Example 9 was used and that 300 mL of 1-butene was used in preparation of a mixed gas.

As a result, 106 g of a propylene/ethylene-butene block copolymer having good particle properties was obtained.

According to the results of CFC-IR, the above obtained block copolymer had a rubber content (CP content) of 8.5% by weight, an MFR of 13.7 (dg/minute), an ethylene content in rubber (CP) of 72% by weight, a weight average molecular weight of the CP portion of 660,000 and an $[\eta]_{cp}$ of 4.42. The propylene homopolymer separately sampled had a Tm of 150.1° C. and an MFR of 18.3 (dg/minute).

Example 11

(1) Block Polymerization by Ethylene-1-Butene Copolymerization

Similar operation to (4) of above Example 1 was conducted except that the same prepolymerized catalyst as used in above Example 9 was used and that 450 mL of 1-butene was used in preparation of a mixed gas.

As a result, 127 g of a propylene/ethylene-butene block copolymer having good particle properties was obtained.

According to the results of CFC-IR, the above obtained block copolymer had a rubber content (CP content) of 6.8% by weight, an MFR of 31.6 (dg/minute), an ethylene content in rubber (CP) of 67% by weight, a weight average molecular weight of the CP portion of 480,000 and an $[\eta]_{cp}$ of 3.48. The propylene homopolymer separately sampled had an MFR of 40.2 (dg/minute).

Example 12

(1) Metallocene Complex: Synthesis of dichloro{1,1'-dimethylsilylene(2-methyl-4-phenylcyclopentadienyl)(2-methyl-4-(4-trimethylsilyl-3,5-dimethylphenyl)-4H-azulenyl)}hafnium A solution (25.4 mL, 36.0 mmol, 1.42M) of t-butyllithium in pentane was added dropwise at −70° C. to a mixed solution of 3,5-dimethyl-4-trimethylsilyl-bromobenzene (4.63 g, 18.0 mmol) in hexane (50 mL)-diisopropyl ether (10 mL) and stirred at −10° C. for one hour. The resultant solution was added with 2-methylazulene (2.49 g, 17.5 mmol, 0.97 eq.), warmed to room temperature and stirred for about one hour, and further added with tetrahydrofuran (10 mL) to obtain a brown uniform solution. The solution was added with N-methylimidazole (0.08 mL), cooled to 0° C. and added dropwise with chlorodimethyl(2-methyl-4-phenyl-2,4-cyclopentadienyl)silane (4.36 g, 17.5 mmol). The obtained solution was warmed to room temperature, stirred for one hour, added with distilled water and extracted with diethyl ether. The organic layer was dried with magnesium sulfate and then had the solvent distilled off under reduced pressure to obtain a crude product (9.32 g) of dimethyl(2-methyl-4-phenyl-2,4-cyclopentadienyl)(2-methyl-4-(4-trimethylsilyl-3,5-dimethylphenyl)-1,4-dihydroazulenyl)silane.

The obtained ligand (9.32 g) was dissolved in diethyl ether (50 mL) and added dropwise at 0° C. with a solution (22 mL, 35.0 mmol, 1.59 M) of n-butyllithium in hexane, stirred at room temperature for 2 hours and then added with toluene (400 mL). The resultant solution was cooled to −60° C., added with hafnium tetrachloride (5.60 g, 17.5 mmol), warmed slowly and stirred at room temperature for 2 hours. The obtained reaction solution was concentrated once, extracted with toluene (80 mL) and concentrated again. The resultant substance was extracted with diisopropyl ether (100 mL) followed by drying and further extracted with a mixed solvent of cyclohexane (20 mL)-pentane (100 mL) followed by drying and then washed with diisopropyl ether (30 mL)-hexane (30 mL), diisopropyl ether (5 mL)-hexane (10 mL), diisopropyl ether (10 mL, 5 mL) and hexane (10 mL, 20 mL) to obtain 0.78 g of the object dichloro{1,1'-dimethylsilylene(2-methyl-4-phenylcyclopentadienyl)(2-methyl-4-(4-trimethylsilyl-3,5-dimethylphenyl)-4H-azulenyl)}hafnium (anti 95%).

$^1$H-NMR (400 MHz, CDCl$_3$) δ0.35 (s, 9H, Ar—Si(CH$_3$)$_3$), 0.87 (s, 3H, Si(CH$_3$)$_2$), 1.01 (s, 3H, Si (CH$_3$)$_2$)$_{2.17}$ (s, 3H, Azu-2-CH$_3$), 2.37 (s, 6H, Ar—CH 3), 2.41 (s, 3H, Cp-2-CH$_3$), 5.00 (d, 1H, Azu-4-H), 5.70 (s, 1H, Azu-3-H), 5.75 (d, 1H, Cp-3-H), 5.93 (m, 2H, Azu-5H, 6H), 6.16 (dd, 1H, Azu-7-H), 6.73 (d, 1H, Azu-8-H), 6.86 (d, 1H, Cp-5-H), 6.98 (s, 2H, arom), 7.35-7.40 (m, 5H, arom).

(2) Prepolymerization with Propylene

A prepolymerized catalyst having a ratio of the polymer to the solid catalyst (the value obtained by dividing the amount of the prepolymerized polymer by the amount of the solid catalyst) of 2.21 was prepared by the similar operation to (3) of Example 1 except that the above complex was used.

(3) Block Polymerization by Ethylene-1-Butene Copolymerization

The similar operation to above Example 9 was conducted except that the prepolymerized catalyst prepared in above (2) was used.

As a result, 111 g of a propylene/ethylene-butene block copolymer having good particle properties was obtained.

According to the results of CFC-IR, the above obtained block copolymer had a rubber content (CP content) of 9.7% by weight, an MFR of 5.7 (dg/minute), an ethylene content in rubber (CP) of 81% by weight, a weight average molecular weight of the CP portion of 690,000 and an $[\eta]_{cp}$ of 4.58. The propylene homopolymer separately sampled had a Tm of 152.4° C. and an MFR of 8.2 (dg/minute).

Example 13

(1) Block Polymerization by Ethylene-1-Butene Copolymerization

The similar operation to above Example 10 was conducted using the same prepolymerized catalyst as used in above Example 12.

As a result, 112 g of a propylene/ethylene-butene block copolymer having good particle properties was obtained.

According to the results of CFC-IR, the above obtained block copolymer had a rubber content (CP content) of 7.8% by weight, an MFR of 6.9 (dg/minute), an ethylene content in rubber (CP) of 62% by weight, a weight average molecular weight of the CP portion of 600,000 and an $[\eta]_p$ of 4.11. The propylene homopolymer separately sampled had a Tm of 152.3° C. and an MFR of 8.8 (dg/minute).

Example 14

(1) Block Polymerization by Ethylene-1-Butene Copolymerization

The similar operation to above Example 11 was conducted using the same prepolymerized catalyst as used in above Example 12.

As a result, 201 g of a propylene/ethylene-butene block copolymer having good particle properties was obtained.

According to the results of CFC-IR, the above obtained block copolymer had a rubber content (CP content) of 6.7% by weight, an MFR of 17.9 (dg/minute), an ethylene content in rubber (CP) of 61% by weight, a weight average molecular weight of the CP portion of 480,000 and an $[\eta]_{cp}$ of 3.43. The propylene homopolymer separately sampled had an MFR of 26.1 (dg/minute).

Example 15

(1) Block Polymerization

The similar operation to above Example 9 was conducted except that 75 mg of the prepolymerized catalyst prepared in (3) of Example 2 was used and 180 mL of hydrogen was used in the former-part step polymerization and that the polymerization time was 45 minutes in the latter-part step polymerization.

As a result, 270 g of a propylene/ethylene-butene block copolymer having good particle properties was obtained.

According to the results of CFC-IR, the above obtained block copolymer had a rubber content (CP content) of 23% by weight, an MFR of 17.9 (dg/minute), an ethylene content in rubber (CP) of 93% by weight, a weight average molecular weight of the CP portion of 690,000 and an $[\eta]_{cp}$ of 4.48. The propylene homopolymer separately sampled had an MFR of 5.67 (dg/minute).

Comparative Example 1

(1) Metallocene Complex

According to the method described in JP-A-2005-336092, dichloro{1,1'-dimethylsilylene(2,3,4,5-tetramethylcyclopentadienyl)(2-ethyl-4-phenyl-4H-azulenyl)}hafnium was synthesized, which was a transition metal complex having a substituent at every position of the cyclopentadienyl part.

(2) Block Polymerization by Ethylene-Propylene Copolymerization

A prepolymerized catalyst was prepared similarly to (2) and (3) of Example 1 except that the above prepared dichloro{1,1'-dimethylsilylene(2,3,4,5-tetramethylcyclopentadienyl)(2-ethyl-4-phenyl-4H-azulenyl)}hafnium was used. The ratio of the polymer to the solid catalyst (the value obtained by dividing the amount of the prepolymerized polymer by the amount of the solid catalyst) was 1.91.

Subsequently, polymerization was carried out similarly to (4) of Example 1 to obtain 7.4 g of a polymer withdrawn at the end of the first-stage polymerization and 23.3 g of a propylene/ethylene-propylene based block copolymer. According to the results of CFC-IR, the obtained propylene/ethylene-propylene based block copolymer had a rubber content (CP content) of 7.2% by weight, an ethylene content in rubber (CP) of 67.3% by mole and a weight average molecular weight of the CP portion of 125,000. The propylene homopolymer separately sampled had a Tm of 154.2° C.

Comparative Example 2

(1) Metallocene Complex

According to the method described in JP-A-2000-95791, dichloro{1,1'-dimethylsilylenebis(2-ethyl-4-(2-fluoro-4-biphenylyl)-4H-azulenyl)}hafnium was synthesized, which was a transition metal complex having C2 symmetry.

(2) Prepolymerization and Block Polymerization by Ethylene-Propylene Copolymerization A prepolymerized catalyst was prepared similarly to (2) and (3) of Example 1 except that dichloro{1,1'-dimethylsilylenebis(2-ethyl-4-(2-fluoro-4-biphenylyl)-4H-azulenyl)}hafnium was used. The ratio of the polymer to the solid catalyst (the value obtained by dividing the amount of the prepolymerized polymer by the amount of the solid catalyst) was 2.22.

Subsequently, polymerization was carried out similarly to (4) of Example 1 to obtain 28.3 g of a polymer withdrawn at the end of the first-stage polymerization and 433 g of a propylene/ethylene-propylene based block copolymer. According to the results of CFC-IR, the obtained propylene/ethylene-propylene based block copolymer had a rubber content (CP content) of 58.6% by weight, an ethylene content in rubber (CP) of 25.8% by mole and a weight average molecular weight of the CP portion of 217,000.

Comparative Example 3

(1) Metallocene Complex

According to the method described in JP-A-2003-231714, dichloro{1,1'-dimethylsilylenecyclopentadienyl(2,4-dimethyl-4H-azulenyl)}hafnium was synthesized, which was a transition metal complex having a structure that the substituent at 4-position of the hydroazulenyl part has carbon atoms less than 6.

(2) Ethylene-Propylene Copolymerization

A catalyst was prepared similarly to (1) of Example 8 except that the complex obtained in above (1) was used. After polymerization was carried out for 60 minutes similarly to (2) of Example 8, ethanol (20 mL) was introduced to stop the polymerization. The reaction solution had the solvent distilled off and dried similarly to obtain 10 g of a polymer. The obtained ethylene-propylene copolymer had an ethylene content of 65.3% by mole and a weight average molecular weight of 72,000.

Comparative Example 4

(1) Metallocene Complex

Dichloro{1,1'-dimethylsilylenebis(2-methyl-4-phenylindenyl)}zirconium was synthesized according to the method described in "Organometallics" vol. 13, p. 954 (1994).

(2) Prepolymerization with Propylene

A prepolymerized catalyst having a multiplying factor of prepolymerization (the value obtained by dividing the amount of the prepolymerized polymer by the amount of the solid catalyst) of 2.07 was prepared similarly to (3) of Example 1 except that the above complex was used.

(3) Block Polymerization by Ethylene-1-Butene Copolymerization

Similar operation to above Example 9 was conducted except that the prepolymerized catalyst (30 mg) prepared in above (2) was used and that 180 mL of hydrogen was used in the former-part step polymerization.

As a result, 203 g of a propylene/ethylene-butene block copolymer having good particle properties was obtained.

According to the results of CFC-IR, the above obtained block copolymer had a rubber content (CP content) of 29% by weight, an MFR of 0.4 (dg/minute), an ethylene content in rubber (CP) of 90% by weight, a weight average molecular weight of the CP portion of 137,000 and an $[\eta]_{cp}$ of 1.30. The propylene homopolymer separately sampled had a Tm of 149.2° C. and an MFR of 0.18 (dg/minute).

Comparative Example 5

(1) Block Polymerization by Ethylene-1-Butene Copolymerization

Similar operation to (3) of above Comparative Example 4 was conducted except that the same prepolymerized catalyst as used in above Comparative Example 4 was used and 300 mL of hydrogen was used in the former-part step polymerization and that 300 mL of 1-butene was introduced to prepare a mixed gas.

As a result, 345 g of a propylene/ethylene-butene block copolymer having good particle properties was obtained.

According to the results of CFC-IR, the above obtained block copolymer had a rubber content (CP content) of 24% by weight, an MFR of 1.4 (dg/minute), an ethylene content in rubber (CP) of 78% by weight, a weight average molecular weight of the CP portion of 120,000 and an $[\eta]_{cp}$ of 1.17. The propylene homopolymer separately sampled had a Tm of 149.4° C. and an MFR of 0.7 (dg/minute).

Comparative Example 6

(1) Block Polymerization by Ethylene-1-Butene Copolymerization

Similar operation to above Comparative Example 4 was conducted except that 50 mg of the same prepolymerized catalyst as used in above Comparative Example 2 was used.

As a result, 127 g of a propylene/ethylene-butene block copolymer having good particle properties was obtained.

According to the results of CFC-IR, the above obtained block copolymer had a rubber content (CP content) of 17% by weight, an MFR of 2.0 (dg/minute), an ethylene content in rubber (CP) of 83% by weight, a weight average molecular weight of the CP portion of 390,000 and an $[\eta]_{cp}$ of 2.91. The propylene homopolymer separately sampled had a Tm of 157.6° C. and an MFR of 3.3 (dg/minute).

Comparative Example 7

(1) Block Polymerization by Ethylene-1-Butene Copolymerization

Similar operation to above Comparative Example 5 was conducted except that 50 mg of the same prepolymerized catalyst as used in above Comparative Example 2 was used.

As a result, 135 g of a propylene/ethylene-butene block copolymer having good particle properties was obtained.

According to the results of CFC-IR, the above obtained block copolymer had a rubber content (CP content) of 18% by weight, an MFR of 1.7 (dg/minute), an ethylene content in rubber (CP) of 67% by weight, a weight average molecular weight of the CP portion of 330,000 and an $[\eta]_{cp}$ of 2.58. The propylene homopolymer separately sampled had a Tm of 157.5° C. and an MFR of 2.3 (dg/minute).

The properties and the like of the polymers of above Examples 1 to 15 and Comparative Examples 1 to 7 are shown in Table 1.

TABLE 1

| Example | Complex | Polymerization method | Comonomer | Polymer yield (g) | Rubber content (wt %) | Ethylene content in rubber (mol %) | Mw(CP) | η | MFR(ICP) (g/10 min) | Tm (° C.) | MFR(Homo) (g/10 min) |
|---|---|---|---|---|---|---|---|---|---|---|---|
| Example 1 | a | Block polymerization | Propylene | 85 | 6.6 | 52 | 320000 | — | 3.4 | 155.6 | 393 |
| Example 2 | b | Block polymerization | Propylene | 86 | 5.2 | 58 | 380000 | — | 55.4 | 150.8 | 77.9 |
| Example 3 | c | Block polymerization | Propylene | 141 | 13.8 | 53.5 | 330000 | — | 5.7 | 152.7 | 9.8 |
| Example 4 | d | Block polymerization | Propylene | 84 | 7.5 | 54.5 | 350000 | — | 31 | 150.9 | 42 |
| Example 5 | e | Block polymerization | Propylene | 121 | 8.9 | 55.2 | 340000 | — | 22 | 150.7 | 35 |
| Example 6 | f | Block polymerization | Propylene | 3 | 26.4 | 70 | 380000 | — | — | — | — |
| Example 7 | g | Block polymerization | Propylene | 47 | 8.6 | 56.5 | 330000 | — | 50.6 | 153.6 | — |
| Example 8 | b | Slurry polymerization | Propylene | 35 | — | 55.6 | 285000 | — | — | — | — |
| Com Ex 1 | i | Block polymerization | Propylene | 23 | 7.2 | 67.3 | 125000 | — | — | 154.2 | — |
| Com Ex 2 | j | Block polymerization | Propylene | 433 | 58.6 | 25.8 | 217000 | — | — | — | — |
| Com Ex 3 | k | Slurry polymerization | Propylene | 10 | — | 65.3 | 72000 | — | — | — | — |
| | | | | (wt %) below | | | | | | | |
| Example 9 | b | Block polymerization | 1-Butene(150 mL) | 110 | 9.5 | 89 | 790000 | 5.10 | 11.6 | 150.2 | 18.3 |
| Example 10 | b | Block polymerization | 1-Butene(300 mL) | 106 | 8.5 | 72 | 660000 | 4.42 | 13.7 | 150.1 | 18.3 |
| Example 11 | b | Block polymerization | 1-Butene(450 mL) | 127 | 6.8 | 67 | 480000 | 3.48 | 31.6 | — | 40.2 |
| Example 12 | h | Block polymerization | 1-Butene(150 mL) | 111 | 9.7 | 81 | 690000 | 4.58 | 5.7 | 152.4 | 8.2 |
| Example 13 | h | Block polymerization | 1-Butene(300 mL) | 112 | 7.8 | 62 | 600000 | 4.11 | 6.9 | 152.3 | 8.8 |
| Example 14 | h | Block polymerization | 1-Butene(450 mL) | 201 | 6.7 | 61.9 | 480000 | 3.43 | 17.9 | — | 26.1 |
| Example 15 | b | Block polymerization | 1-Butene(150 mL) | 270 | 22.9 | 93 | 690000 | 4.48 | 17.9 | — | 5.67 |

TABLE 1-continued

| Example | Complex | Polymerization method | Comonomer | Polymer yield (g) | Rubber content (wt %) | Ethylene content in rubber (mol %) | Mw(CP) | η | MFR(ICP) (g/10 min) | Tm (° C.) | MFR(Homo) (g/10 min) |
|---|---|---|---|---|---|---|---|---|---|---|---|
| Com Ex 4 | l | Block polymerization | 1-Butene(150 mL) | 203 | 29 | 90 | 137000 | 1.30 | 0.4 | 149.2 | 0.18 |
| Com Ex 5 | l | Block polymerization | 1-Butene(300 mL) | 345 | 24 | 78 | 120000 | 1.17 | 1.4 | 149.4 | 1.4 |
| Com Ex 6 | j | Block polymerization | 1-Butene(150 mL) | 127 | 17 | 83 | 390000 | 2.91 | 2 | 157.6 | 3.3 |
| Com Ex 7 | j | Block polymerization | 1-Butene(300 mL) | 135 | 18 | 67 | 330000 | 2.58 | 1.7 | 157.5 | 2.3 |

Structure of Complex
a: $Me_2Si(2,3,5-Me_3Cp)(2Me4Ph4HAzu)HfCl_2$
b: $Me_2Si(2Me4PhCp)(2Me4Ph4HAzu)HfCl_2$
c: $Me_2Si[2Me4(3,6Me_2Ph)Cp](2Me4Ph4HAzu)HfCl_2$
d: $Me_2Si[2Me4(4-1BuPh)Cp](2Me4Ph4HAzu)HfCl_2$
e: $Me_2Si(2Me4PhCp)(2Et4Ph4HAzu)HfCl_2$
f: $Me_2Si(2Me4tBuCp)(2Me4Ph4HAzu)HfCl_2$
g: $Me_2Si(2Me4iPrCp)2Me4Ph4HAzu)HfCl_2$
h: $Me_2Si(2Me4PhCp)[2Me4(4TMS-3,5Me_2Ph)4HAzu]HfCl_2$
i: $Me_2Si(2,3,4,5-Me_4Cp)(2Me4Ph4HAzu)HfCl_2$
j: $Me_2Si[2Et4(2-F-4-Biphenylyl)4HAzu]_2HfCl_2$
k: $Me_2Si(Cp)(2,4Me_4HAzu)HfCl_2$
l: $Me_2Si(2Me4PhInd)_2ZrCl_2$ Evaluation Study on the Results of Examples and Comparative Examples Examination and comparison of each example and each comparative example show that the present invention provides a copolymer having a higher ethylene content and a higher molecular weight than the case using a transition metal compound of comparative examples with the same gas composition. It is clarified, therefore, that a new transition metal compound having a specific structure represented by the general formula and a catalyst composed of the transition metal compound in the present invention can provide well-balanced reactivity between ethylene and an α-olefin having 3 to 20 carbon atoms and a copolymer of a high molecular weight.

With regard to each comparative example where the transition metal compound of the present invention is not used for the catalyst, Comparative Examples 1 and 3 give a lower molecular weight copolymer and Comparative Example 2 does not give a desired ethylene content. Further, any of Comparative Examples 4 to 7 gives a low molecular weight copolymer in ethylene-butene copolymerization.

Consequently, it is clarified that the conditions constituting the present invention are reasonable and significant and the present invention is advantageous over conventional technologies.

The new transition metal compound of the present invention, the catalyst for olefin polymerization containing the transition metal compound and the method for producing propylene/ethylene-α-olefin block copolymer using the catalyst are extremely useful in efficiently producing a propylene/ethylene-α-olefin block copolymer of high MFR that can be used in molding fields such as injection molding, injection compression molding and fiber forming, and the propylene/ethylene-α-olefin block copolymer is suitable for a general injection material such as sundries, an automobile material such as a bumper and an instrument panel, a material for home electrical appliances such as a housing of a refrigerator and a vacuum cleaner, a transparent food-wrapping material such as a container for jelly, an impact-resistant food-wrapping material such as a container for yoghurt, a heat-resistant food-wrapping material such as a container for cup noodles, a fiber material such as nonwoven fabric for a sanitary article, a flexible fiber material such as a supporter and the like.

What is claimed is:

1. A transition metal compound (A) represented by the following general formula:

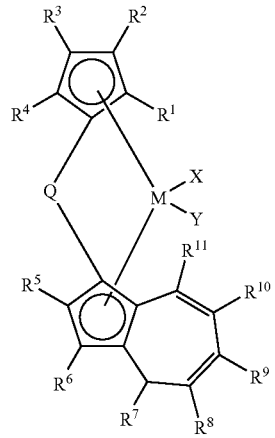

wherein, $R^1$, $R^2$, $R^3$, $R^4$, $R^5$ and $R^6$ each independently are a hydrogen atom, a hydrocarbon group, a silicon-containing hydrocarbon group or a halogenated hydrocarbon group; however, any two of $R^1$, $R^2$, $R^3$ and $R^4$ are a substituent other than a hydrogen atom and any two of $R^1$, $R^2$, $R^3$ and $R^4$ are a hydrogen atom; further, adjacent $R^1$, $R^2$, $R^3$ and $R^4$ do not form a ring with each other; $R^7$ is a hydrocarbon group, a halogenated hydrocarbon group or a silicon-containing hydrocarbon group each having 6 or more carbon atoms; $R^8$, $R^9$, $R^{10}$ and $R^{11}$ each independently are a hydrogen atom, a hydrocarbon group, a silicon-containing hydrocarbon group or a halogenated hydrocarbon group; Q is a substituted silylene group or a substituted germylene group; X and Y each independently are a ligand that forms a σ-bond with M; and M is a transition metal of the group 4 of the periodic table.

2. The transition metal compound (A) according to claim 1 wherein $R^1$ and $R^3$ are a substituent other than a hydrogen atom.

3. A catalyst for olefin polymerization comprising the transition metal compound (A) according to claim 1.

4. The catalyst for olefin polymerization according to claim 3 further comprising a component (B) or both the component (B) and a component (C); wherein
component (B) is a compound selected from the group consisting of an organic aluminum oxy compound and an ionic compounds or a Lewis acid that reacts with the component (A) and can change the component (A) to a cationic complex; and
component (C) is a fine particle support.

5. The catalyst for olefin polymerization according to claim 3 further comprising a component (D) or both the component (D) and a component (E); wherein
component (D) is a compound selected from the group consisting of an ion-exchangeable layered compound and an inorganic silicate; and
component (E) is an organoaluminum compound.

6. A method for producing an α-olefin polymer or copolymer comprising contacting the catalyst for olefin polymerization according to claim 3 with an olefin.

7. A method for producing a propylene/ethylene-α-olefin block copolymer where multistage polymerization is continuously carried out in the presence of a catalyst for olefin polymerization, the method comprising producing a crystalline propylene polymer component in the presence of the catalyst for olefin polymerization according to claim 3, and subsequently producing copolymer components of ethylene and at least one comonomer selected from α-olefins having 3 to 20 carbon atoms by a gas phase polymerization in the presence of a crystalline propylene polymer component.

8. The method for producing a propylene/ethylene-α-olefin block copolymer according to claim 7 wherein the comonomer is propylene.

9. The method for producing a propylene/ethylene-α-olefin block copolymer according to claim 7 wherein the comonomer is selected from the group consisting of 1-butene, 1-hexene and 1-octene.

10. The transition metal compound (A) according to claim 1, wherein any two of $R^1$, $R^2$, $R^3$ and $R^4$ represent a substituent selected from the group consisting of an alkyl group having 1-6 carbon atoms and an aryl group having up to 12 carbon atoms, and wherein any two of $R^1$, $R^2$, $R^3$ and $R^4$ are a hydrogen atom.

11. The transition metal compound (A) according to claim 1, wherein $R^1$ and $R^3$ represent a substituent selected from the group consisting of an alkyl group having 1-6 carbon atoms and an aryl group having up to 12 carbon atoms, and wherein $R^2$ and $R^4$ are a hydrogen atom.

12. The transition metal compound (A) according to claim 1, wherein any two of $R^1$, $R^2$, $R^3$ and $R^4$ represent a substituent selected from the group consisting of an alkyl group having 2-6 carbon atoms and an aryl group having up to 12 carbon atoms, and wherein any two of $R^1$, $R^2$, $R^3$ and $R^4$ are a hydrogen atom.

13. The transition metal compound (A) according to claim 1, wherein $R^1$ and $R^3$ represent a substituent selected from the group consisting of an alkyl group having 2-6 carbon atoms and an aryl group having up to 12 carbon atoms, and wherein $R^2$ and $R^4$ are a hydrogen atom.

14. The transition metal compound (A) according to claim 1, wherein any two of $R^1$, $R^2$, $R^3$ and $R^4$ represent a substituent selected from the group consisting of an alkyl group having 3-6 carbon atoms and an aryl group having up to 12 carbon atoms, and wherein any two of $R^1$, $R^2$, $R^3$ and $R^4$ are a hydrogen atom.

15. The transition metal compound (A) according to claim 1, wherein $R^1$ and $R^3$ represent a substituent selected from the group consisting of an alkyl group having 3-6 carbon atoms and an aryl group having up to 12 carbon atoms, and wherein $R^2$ and $R^4$ are a hydrogen atom.

* * * * *